US008679740B2

(12) United States Patent
Kwong et al.

(10) Patent No.: US 8,679,740 B2
(45) Date of Patent: Mar. 25, 2014

(54) METHODS FOR AMPLIFYING HEPATITIS C VIRUS NUCLEIC ACIDS

(75) Inventors: Ann Dak-Yee Kwong, Cambridge, MA (US); James Daniel Frantz, Belmont, MA (US); Douglas John Bartels, North Liberty, IA (US); Chao Lin, Winchester, MA (US); Benjamin Shames, Arlington, MA (US); Sheila Seepersaud, Acton, MA (US); Judith A. Lippke, Chestnut Hill, MA (US); Tara Lynn Kieffer, Brookline, MA (US); Yi Zhou, Lexington, MA (US); Eileen Z. Zhang, Andover, MA (US); James C. Sullivan, Sudbury, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/186,985

(22) Filed: Jul. 20, 2011

(65) Prior Publication Data
US 2012/0129155 A1 May 24, 2012

Related U.S. Application Data

(63) Continuation of application No. PCT/US2010/021589, filed on Jan. 21, 2010.

(60) Provisional application No. 61/146,083, filed on Jan. 21, 2009.

(51) Int. Cl.
*C12Q 1/70* (2006.01)
*C12Q 1/68* (2006.01)
*C12P 19/34* (2006.01)

(52) U.S. Cl.
USPC ............................. 435/5; 435/6.12; 435/91.2

(58) Field of Classification Search
USPC .......... 435/6.12, 91.2; 536/24.3, 24.32, 24.33
See application file for complete search history.

(56) References Cited

U.S. PATENT DOCUMENTS

| 5,427,909 | A * | 6/1995 | Okamoto et al. ................. 435/5 |
| 6,153,421 | A * | 11/2000 | Yanagi et al. ............. 435/235.1 |
| 6,790,952 | B2 * | 9/2004 | Groen et al. ............... 536/24.33 |
| 2004/0137539 | A1 | 7/2004 | Bradford | |
| 2004/0229817 | A1 | 11/2004 | Duggal et al. | |
| 2005/0282179 | A1 | 12/2005 | Martin et al. | |

FOREIGN PATENT DOCUMENTS

EP 0633321 A1 1/1995

OTHER PUBLICATIONS

Rychlik et al., Nucleic Acids Research 17(21), 8543-8551 (1989).*
International Search Report from corresponding International Application No. PCT/US2010/021589.

Ramachandran, R., et al., "Anti-viral activity of VX-950 resolves expression of an HCV-associated gene signature," Journal of Hepatology, vol. 44, No. Sup2, Apr. 2006, p. S223, XP002565761 (abstract).
Helbig, K.J., et al., "Analysis of ISG expression in chronic hepatitis C identified viperin as a potential antiviral effector," Hapatology, vol. 42, 2005, pp. 702-710, XP002565762.
Girard, S., et al., "An altered cellular response to interferon and up-regulation of interleukin-8 induced by the hepatitis C viral protein NS5A uncovered by microarray analysis," Virology, vol. 295, 2002, pp. 272-283, XP002565763.
Iizuka, N., et al. "Differential gene expression in distinct virologic types of hepatocellular carcinoma: association with liver cirrhosis," Oncogene, vol. 22, 2003, pp. 3007-3014, XP002565764.
Girard, S., et al., "Hepatitis C virus NS5A-regulated gene expression and signaling revealed via icroarray and comparative promoter analysis," Heptatology, vol. 40, 2004, pp. 708-718, XP0024565765.
Su, A.I., et al., "Genomic analysis of the host response to hepatitis C virus infection," Proceedings of the National Academy of Sciences, vol. 99, No. 24, Nov. 26, 2002, pp. 15669-15674, XP002565766.
Perni, R.B., et al., "Preclinical profile of VX-950, a potent, selective, and orally bioavailable inhibitor of hepatitis C virus NS3-4A serine protease," Antimicrobial Agents and Chemotherapy, vol. 50, No. 3, Mar. 2006, pp. 899-909, XP002565767.
Reesink, H.W., et al., "Rapid decline of viral RNA in hepatitis C patients treated with VX-950: a phase Ib, placebo-controlled, randomized study," Gastroenterology, vol. 131, Oct. 2006, pp. 997-1002, XP002565768.
Graham, D.J., et al., "A genotype 2b NS5B polymerase with novel substitutions supports replication of a chimeric HCV 1b:2b replicon containing a genotype 1b NS3-5A background", Antiviral Research, Elsevier BV, NL LNKD-DOI:10.1016/J.Antiviral.2005.08.005, vol. 69, No. 1, Jan. 1, 2006, pp. 24-30, XP025031334.
Mao, et al., "Colorimetric oligonucleotide array for genotyping of hepatitis C virus based on the 5' non-coding region" Clinica Chimca Acta, Elsevier BV, Amsterdam NL LNKD-DO:10.1016/J.CCA.

(Continued)

*Primary Examiner* — Kenneth Horlick
(74) *Attorney, Agent, or Firm* — Lisa A. Dixon; Booyong S. Lim

(57) ABSTRACT

A method of amplifying an HCV nucleic acid in an HCV infected sample comprises amplifying a segment of a DNA template that is complementary to a genome of HCV RNA from the sample by a two-stage PCR, wherein a first stage PCR employs a first outer primer and a second outer primer, and a second stage PCR employs a first inner primer and a second inner primer. The nucleotide sequence of the first outer primer comprises a nucleotide sequence as set forth in SEQ ID NO: 2; or SEQ ID NO:9, wherein optionally 1, 2 or 3 nucleotides are other nucleotides than those of SEQ ID NO: 9. The nucleotide sequence of the second outer primer comprises a nucleotide sequence set forth in SEQ ID NO: 3 or 4; or a nucleotide sequence as set forth in SEQ ID NO: 10 or 11, wherein optionally 1, 2 or 3 nucleotides are other nucleotides than those of SEQ ID NO: 10 and 11. The nucleotide sequence of the first inner primer comprises a nucleotide sequence as set forth in SEQ ID NO: 5; or SEQ ID NO:12, wherein optionally 1, 2 or 3 nucleotides are other nucleotides than those of SEQ ID NO: 12. The nucleotide sequence of the second inner primer comprises a nucleotide sequence as set forth in SEQ ID NO: 6 or 7; or a nucleotide sequence as set forth in SEQ ID NO: 13 or 14, wherein optionally 1, 2 or 3 nucleotides are other nucleotides than those of SEQ ID NO: 13 and 14.

21 Claims, 4 Drawing Sheets

(56) References Cited

OTHER PUBLICATIONS 2007.09.009, vol. 388, No. 1-2, Dec. 19, 2007, pp. 22-27, XP022394595.

Lin, Chao, etal., "In vitro studies of cross-resistance mutations against two hepatitis C virus serine protease inhibitors, VX-950 and BILN2061" Journal of Biological Chemistry, American Society for Biochemistry and Molecular Biology, Inc., US LNKD-DOI:10.1074/JBC.M506462200, vol. 280, No. 44, Nov. 4, 2005, pp. 36784-36791, XP002441097.

Thiers, V., et al., "Development of a simple restriction fragment length polymorphism (RFLP) based assay for HCV genotyping and comparative analysis with genotyping and serotyping tests", Journal of Virological Methods, Elsevier BV, NL, vol. 65, No. 1, Apr. 1997, pp. 9-17, XP026831787.

Hoshida, Y. et al. "Hepatitis C Virus Core Protein and Hepatitis Activity Are Associated Through Transactivation of Interleukin-8", J Infect Dis. vol. 192, No. 2, pp. 266-275, (2005).

Adiwijaya, B.S., et al., Rapid decrease of wild-type hepatitis C virus on telaprevir treatment, Antiviral therapy, 2009, 14:591-595.

Aizaki, H., et al., Full-length complementary DNA of hepatitis C virus genome from an infectious blood sample, Hepatology, 1998, 27:621-627.

Fan, X., et al., Efficient amplification and cloning of near full-length hepatitis C virus genome from clinical samples, Biochemical and Biophysical Research Communications, 2006, 346:1163-1172.

Henke, W., et al., Betaine improves the PCR amplification of GC-rich DNA sequences, Nucleic Acids Research 1997, 25:3957-3958.

Kwong, A.D., et al., Sequence and phenotypic analysis for resistance monitoring in hepatitis C virus drug development: recommendations from the HCV DRAG, Gastroenterology, 2011, 140:755-760.

Liu, Z., et al., Accurate representation of the hepatitis C virus quasispecies in 5.2-kilobase amplicons, Journal of Clinical Microbiology, 2004, 42:4223-4229.

Lu, L., et al., a refined long RT-PCR technique to amplify complete viral RNA genome sequences from clinical samples: application to a novel hepatitis C virus variant of genotype 6, Journal of Virological Methods, 2005, 126:139-148.

Rees, W.A., et al., Betaine can eliminate the base pair composition dependence of DNA melting, Biochemistry, 1993, 32:137-144.

Simmonds, P., Genetic diversity and evolution of hepatitis C virus 1— 15 years on, The Journal of General Virology, 2004, 85:3173-3188.

Tellier, R., et al., Long PCR and its application to hepatitis viruses: amplification of hepatitis A, hepatitis B, and hepatitis C virus genomes, Journal of Clinical Microbiology, 1996, 34:3085-3091.

Xu, Z., et al., Comparative analysis of nearly full-length hepatitis C virus quasispecies from patients experiencing viral breakthrough during antiviral therapy: clustered mutations in three functional genes, E2, NS2, and NS5a, Journal of Virology, 2008, 82:9417-9424.

Zhou, D., et al., Separation of near full-length hepatitis C virus quasispecies variants from a complex population, Journal of Virological Methods, 2007, 141:220-224.

Kuntzen, T., et al., A Set of Reference Sequences for the Hepatitis C Genotypes for the Hepatitis C Genotypes 4d, 4f, and 4k Covering the Full Open Reading Frame, Journal of Medical Virology 80:1370-1378 (20008).

Yanagi, M., et al., Transcripts from a single full-length cDNA clone of hepatitis C virus are infectious when directly transfected into the liver of a chimpanzee, Medical Sciences, vol. 94, pp. 8738-8743, Aug. 1997.

\* cited by examiner

SEQUENCE LISTING

```
<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: misc_feature
<222> LOCATION: (1)..(26)
<223> OTHER INFORMATION: This region may encompass 1 to 26 nucleotides

<400> SEQUENCE: 1
aaaaaaaaaa aaaaaaaaaa aaaaaaaaaa                                            30

<210> SEQ ID NO 2
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
gagtagtgtt gggtcg                                                           16
```

```
<210> SEQ ID NO 3
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
cacgctgtga taaatg                                                       16

<210> SEQ ID NO 4
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
cavgctgtga tatatg                                                       16

<210> SEQ ID NO 5
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
ggtgcttgcg agtgcc                                                       16

<210> SEQ ID NO 6
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
tagccagccg tgaacc                                                       16

<210> SEQ ID NO 7
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
tarccagcra cgaacc                                                       16

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
```
aaaaaaaaaa aaaaaaaaaa                                               20

<210> SEQ ID NO 9
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
caagactgct agccgagtag tgttgggtcg                                    30

<210> SEQ ID NO 10
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
ccgggcayga gacacgctgt gataaatg                                      28

<210> SEQ ID NO 11
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
tcgggcacga gacavgctgt gatatatg                                      28

<210> SEQ ID NO 12
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
gtactgcctg atagggtgct tgcgagtgcc                                    30

<210> SEQ ID NO 13
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
tctcccccgc tgtagccagc cgtgaacc                                      28

<210> SEQ ID NO 14
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14 tctccccgc tgtarccagc racgaacc                                              28

<210> SEQ ID NO 15
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
aagtactgcc tgatagggtg cttgcgagtg cc                                        32

<210> SEQ ID NO 16
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16 atctccccg ctgtagccag ccgtgaacc                                             29

<210> SEQ ID NO 17
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17 atctccccg ctgtarccag cracgaacc                                             29

METHODS FOR AMPLIFYING HEPATITIS C VIRUS NUCLEIC ACIDS

RELEVANT APPLICATION(S)

This application is a continuation of PCT Application Number PCT/US2010/021589, filed Jan. 21, 2010 which claims priority to U.S. Provisional Application No. 61/146,083, filed on Jan. 21, 2009. The entire teachings of these applications are incorporated herein by reference.

SEQUENCE LISTING

The instant application contains a Sequence Listing submitted concurrently herewith via EFS-Web and is hereby incorporated by reference in its entirety. Said ASCII copy, created on Mar. 25, 2010, is named VPI08120.txt and is 4,614 bytes in size.

BACKGROUND OF THE INVENTION

Hepatitis C Virus (HCV) is a positive sense single-strand RNA virus in the family of flavirividae. HCV is a major cause of chronic liver disease worldwide, and remains one of the most common causes of post-transfusion non-A, non-B hepatitis. Of persons who become infected with HCV, 20-25% may be able to clear the virus after the acute infection, but 75-80% will develop chronic Hepatitis C infection. (See, e.g., preface, *Frontiers in Viral Hepatitis*, Ed. R. F. Chinazi, J.-P. Sommadossi, and C. M. Rice, p. xi., Elsevier (2003)). This usually results in recurrent and progressively worsening liver inflammation, which often leads to more severe states, such as cirrhosis and hepatocellular carcinoma.

Obtaining information of, and quantifying, the HCV genome can facilitate development of a number of approaches for diagnosing and/or treating HCV infection in patients. Generally, analysis of a relatively long fragment of the HCV genome would provide more sequence information which cannot be obtained from multiple, relatively shorter fragments. However, it generally has been difficult to amplify long RNA genomes (e.g., having over 5 kilobases) that require a reverse transcription (RT) step prior to PCR amplification with conventional polymerase chain reactions (PCRs). Such situations are even more challenging when trying to amplify an HCV genome having, for example, greater than 8,000 base pairs, or full-length HCV genome. Also, it has generally been difficult to amplify such a long HCV genome from specimens obtained from clinical and epidemiological studies with relatively high reproducibility.

Therefore, there is a need for new amplification and assay methods of an HCV genome. In particular, there is a need for new amplification and assay methods of an HCV nucleic acid having greater than 8,000 base pairs (e.g., full-length HCV) with relatively high reproducibility (e.g., greater than 80%, greater than 85%, or greater than 90%).

SUMMARY OF THE INVENTION

The present invention generally provides methods of amplifying an HCV nucleic acid, methods of assaying an HCV nucleic acid, kits and primers therefor.

In one aspect, the present invention provides a method of amplifying a hepatitis C virus (HCV) nucleic acid from an HCV-infected sample. The method comprises amplifying a segment of a DNA template that is complementary to a genome of HCV RNA from the sample by a two-stage polymerase chain reaction (PCR), wherein a first stage PCR employs a first outer primer and a second outer primer, and a second stage PCR employs a first inner primer and a second inner primer. In one embodiment, the method further comprises forming the DNA template that is complementary to a genome of HCV RNA from the sample by reverse transcription (RT) using an RT primer.

In another aspect, the present invention provides a method of assaying a hepatitis C virus (HCV) nucleic acid from an HCV infected sample. The method comprises amplifying a segment of a DNA template that is complementary to a genome of HCV RNA from the sample by a two-stage polymerase chain reaction (PCR), wherein a first stage PCR employs a first outer primer and a second outer primer, and a second stage PCR employs a first inner primer and a second inner primer. The method further comprises sequencing the amplified HCV nucleic acid. In one embodiment, the method further comprises forming the DNA template that is complementary to a genome of HCV RNA from the sample by reverse transcription (RT) using an RT primer.

In yet another aspect, the present invention provides a kit for amplifying and/or assaying an HCV nucleic acid in an HCV infected sample. In one embodiment, the kit comprises a pair of outer PCR primers comprising a first outer primer and a second outer primer. In another embodiment, the kit comprises a pair of inner PCR primers comprising a first inner primer and a second inner primer. In yet another embodiment, the kit comprises an RT primer, a pair of outer PCR primers comprising a first outer primer and a second outer primer, and a pair of inner PCR primers comprising a first inner primer and a second inner primer.

In one embodiment, the nucleotide sequence of the RT primer comprises SEQ ID NO: 1; the nucleotide sequence of the first outer primer comprises SEQ ID NO: 2; the nucleotide sequence of the second outer primer comprises SEQ ID NO: 3 or SEQ ID NO: 4; the nucleotide sequence of the first inner primer comprises SEQ ID NO: 5; and the nucleotide sequence of the second inner primer comprises SEQ ID NO: 6 or SEQ ID NO: 7:

```
5'-(A)_n-AAAA-3',                    (SEQ ID NO: 1)
where n is an integer of 1-26;

5'-GAGTAGTGTTGGGTCG-3';              (SEQ ID NO: 2)

5'-CACGCTGTGATAAATG-3';              (SEQ ID NO: 3)

5'-CAVGCTGTGATATATG-3';              (SEQ ID NO: 4)

5'-GGTGCTTGCGAGTGCC-3';              (SEQ ID NO: 5)

5'-TAGCCAGCCGTGAACC-3';              (SEQ ID NO: 6)
and

5'-TARCCAGCRACGAACC-3',              (SEQ ID NO: 7)
wherein V is A, C or G; and R is
A or G.
```

In another embodiment, the nucleotide sequence of the RT primer comprises SEQ ID NO: 1 at its 3' end; the nucleotide sequence of the first outer primer comprises at its 3' end a nucleotide sequence as set forth SEQ ID NO: 9, wherein optionally one, two or three nucleotides thereof independently are other nucleotides than those of SEQ ID NO: 9; the nucleotide sequence of the second outer primer comprises at its 3' end a nucleotide sequence as set forth SEQ ID NO: 10 or SEQ ID NO: 11, wherein optionally one, two or three nucleotides thereof independently are other nucleotides than those of EQ ID NO: 10 and SEQ ID NO: 11; the nucleotide sequence of the first inner primer comprises at its 3' end a nucleotide sequence as set forth SEQ ID NO: 12, wherein optionally one, two or three nucleotides thereof independently are other nucleotides than those of SEQ ID NO: 12; the nucleotide sequence of the second inner primer comprises at its 3' end a nucleotide sequence as set forth SEQ ID NO: 13 or SEQ ID NO: 14, wherein optionally one, two or three nucleotides thereof independently are other nucleotides than those of SEQ ID NO: 13 and SEQ ID NO: 14:

```
                                              (SEQ ID NO: 1)
5'-(A)n-AAAA-3',
where n is an integer of 1-26;

(SEQ ID NO: 9)
5'-CAAGACTGCTAGCCGAGTAGTGTTGGGTCG-3';

(SEQ ID NO: 10)
5'-CCGGGCAYGAGACACGCTGTGATAAATG-3';

(SEQ ID NO: 11)
5'-TCGGGCACGAGACAVGCTGTGATATATG-3';

(SEQ ID NO: 12)
5'-GTACTGCCTGATAGGGTGCTTGCGAGTGCC-3';

(SEQ ID NO: 13)
5'-TCTCCCCCGCTGTAGCCAGCCGTGAACC-3';
and (SEQ ID NO: 14)
5'-TCTCCCCCGCTGTARCCAGCRACGAACC-3',
wherein V is A, C or G; R is A or G; and Y is C,
T or U.
```

In yet another embodiment, the nucleotide sequence of the RT primer comprises SEQ ID NO: 1 at its 3' end; the nucleotide sequence of the first outer primer comprises at its 3' end a nucleotide sequence as set forth SEQ ID NO: 9, wherein optionally one, two or three nucleotides thereof independently are other nucleotides than those of SEQ ID NO: 9; the nucleotide sequence of the second outer primer comprises at its 3' end a nucleotide sequence as set forth SEQ ID NO: 10 or SEQ ID NO: 11, wherein optionally one, two or three nucleotides thereof independently are other nucleotides than those of EQ ID NO: 10 and SEQ ID NO: 11; the nucleotide sequence of the first inner primer comprises at its 3' end a nucleotide sequence as set forth SEQ ID NO: 15, wherein optionally one, two or three nucleotides thereof independently are other nucleotides than those of SEQ ID NO: 15; the nucleotide sequence of the second inner primer comprises at its 3' end a nucleotide sequence as set forth SEQ ID NO: 16 or SEQ ID NO: 17, wherein optionally one, two or three nucleotides thereof independently are other nucleotides than those of SEQ ID NO: 16 and SEQ ID NO: 17:

```
                                              (SEQ ID NO: 1)
5'-(A)n-AAAA-3',
where n is an integer of 1-26;

(SEQ ID NO: 9)
5'-CAAGACTGCTAGCCGAGTAGTGTTGGGTCG-3';

(SEQ ID NO: 10)
5'-CCGGGCAYGAGACACGCTGTGATAAATG-3';

(SEQ ID NO: 11)
5'-TCGGGCACGAGACAVGCTGTGATATATG-3';

(SEQ ID NO: 15)
5'-AAGTACTGCCTGATAGGGTGCTTGCGAGTGCC-3';

(SEQ ID NO: 16)
5'-ATCTCCCCCGCTGTAGCCAGCCGTGAACC-3';
and (SEQ ID NO: 17)
5'-ATCTCCCCCGCTGTARCCAGCRACGAACC-3',
wherein V is A, C or G; R is A or G; and Y is C,
T or U.
```

In yet another embodiment, the nucleotide sequence of the RT primer comprises SEQ ID NO: 1; the nucleotide sequence of the first outer primer comprises a nucleotide sequence as set forth in SEQ ID NO: 9, wherein optionally one, two or three nucleotides at positions 1 through 14 from the 5' end of SEQ ID NO:9 are independently other nucleotides than those of SEQ ID NO:9; the nucleotide sequence of the second outer primer comprises a nucleotide sequence set forth in SEQ ID NO: 10 or 11, wherein optionally one, two or three nucleotides at positions 1 through 12 from the 5' end of SEQ ID NOs: 10 and 11 are independently other nucleotides than those of SEQ ID NOs: 10 and 11; the nucleotide sequence of the first inner primer comprises a nucleotide sequence as set forth in SEQ ID NO: 12, wherein optionally one, two or three nucleotides at positions 1 through 14 from the 5' end of SEQ ID NO:12 are independently other nucleotides than those of SEQ ID NO:12; and the nucleotide sequence of the second inner primer comprises a nucleotide sequence set forth in SEQ ID NO: 13 or 14, wherein optionally one, two or three nucleotides at positions 1 through 12 from the 5' end of SEQ ID NOs: 13 and 14 are independently other nucleotides than those of SEQ ID NOs: 13 and 14.

In yet another embodiment, the nucleotide sequence of the RT primer comprises SEQ ID NO: 8; the nucleotide sequence of the first outer primer comprises SEQ ID NO: 9; the nucleotide sequence of the second outer primer comprises SEQ ID NO: 10 or SEQ ID NO: 11; the nucleotide sequence of the first inner primer comprises SEQ ID NO: 12; and the nucleotide sequence of the second inner primer comprises SEQ ID NO: 13 or SEQ ID NO: 14:

```
                                              (SEQ ID NO: 8)
5'-AAAAAAAAAAAAAAAAAAAA-3';

(SEQ ID NO: 9)
5'-CAAGACTGCTAGCCGAGTAGTGTTGGGTCG-3';

(SEQ ID NO: 10)
5'-CCGGGCAYGAGACACGCTGTGATAAATG-3';

(SEQ ID NO: 11)
5'-TCGGGCACGAGACAVGCTGTGATATATG-3';

(SEQ ID NO: 12)
5'-GTACTGCCTGATAGGGTGCTTGCGAGTGCC-3';

(SEQ ID NO: 13)
5'-TCTCCCCCGCTGTAGCCAGCCGTGAACC-3';

(SEQ ID NO: 14)
5'-TCTCCCCCGCTGTARCCAGCRACGAACC-3',
wherein V is A, C or G; R is A or G; and Y is C,
T or U.
```

In yet another embodiment, the nucleotide sequence of the RT primer comprises SEQ ID NO: 8; the nucleotide sequence of the first outer primer comprises SEQ ID NO: 9; the nucleotide sequence of the second outer primer comprises SEQ ID NO: 10 or SEQ ID NO: 11; the nucleotide sequence of the first inner primer comprises SEQ ID NO: 15; and the nucleotide sequence of the second inner primer comprises SEQ ID NO: 16 or SEQ ID NO: 17:

```
5'-AAAAAAAAAAAAAAAAAAAA-3';                          (SEQ ID NO: 8)

5'-CAAGACTGCTAGCCGAGTAGTGTTGGGTCG-3';                (SEQ ID NO: 9)

5'-CCGGGCAYGAGACACGCTGTGATAAATG-3';                  (SEQ ID NO: 10)

5'-TCGGGCACGAGACAVGCTGTGATATATG-3';                  (SEQ ID NO: 11)

5'-AAGTACTGCCTGATAGGGTGCTTGCGAGTGCC-3';              (SEQ ID NO: 15)

5'-ATCTCCCCCGCTGTAGCCAGCCGTGAACC-3';                 (SEQ ID NO: 16)

5'-ATCTCCCCCGCTGTARCCAGCRACGAACC-3',                 (SEQ ID NO: 17)
wherein V is A, C or G; R is A or G; and Y is C,
T or U.
```

The present invention can be used for amplification of HCV nucleic acid from, for example, clinical isolates, such as those derived from the tissue of a patient infected with HCV. With the present PCR methods, an HCV genomic sequences having, for example, greater than 8,000 base pairs can be amplified and sequenced with relatively high reproducibility, e.g., greater than 80%, greater than 85%, or greater than 90% successful rate, even with HCV samples of $10^3$ to $10^4$ IU/ml. The PCR methods of the invention can also be employed for amplifying and sequencing of an HCV genome in HCV samples of less than $10^3$ IU/ml. The sequence information of the HCV genome can be used for development of diagnosing and/or treating HCV infection in patients, and also for other various experimental purposes, for example, generating vectors comprising the HCV genome or a fragment thereof. For example, the present invention can be employed for monitoring or following-up an HCV patient's resistance profile, or response (e.g., exhibiting a particular polymorphism) to a particular therapy; and for a diagnosis kit therefor.

DETAILED DESCRIPTION OF THE INVENTION

The present invention provides methods and kits useful for amplifying, assaying, identifying, sequencing and/or quantifying particular nucleic acid sequences of HCV nucleic acid molecules.

Figure 1:
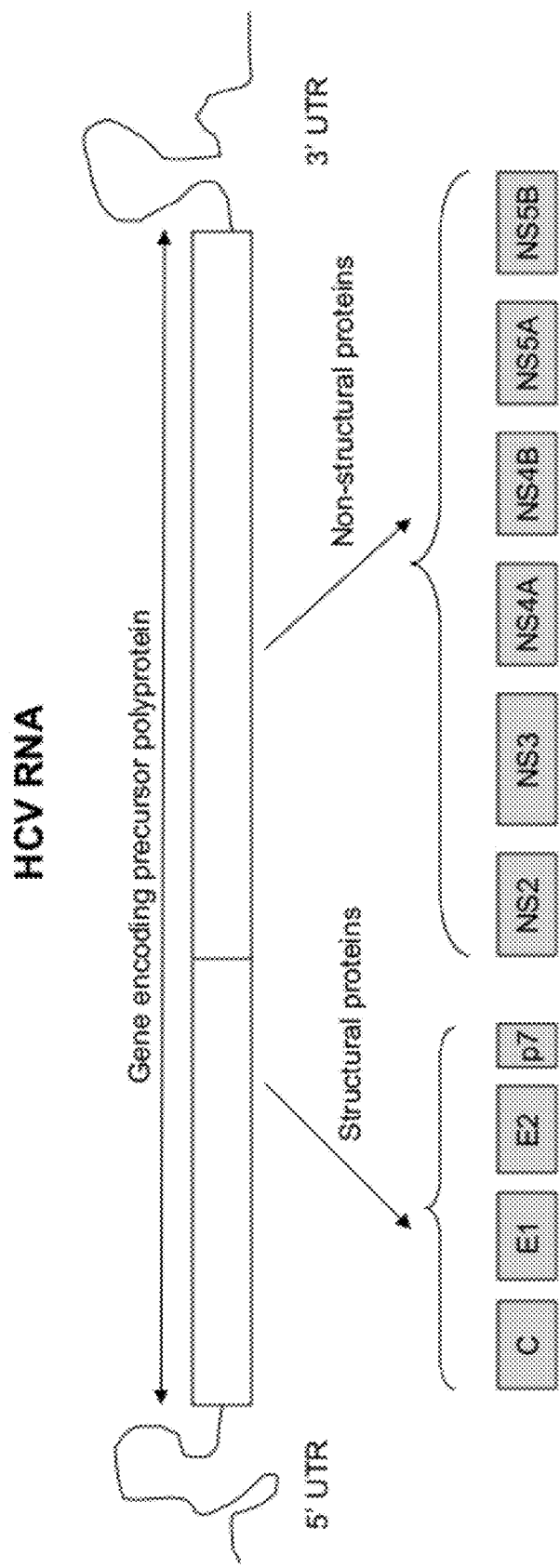
FIG. 1 is a schematic drawing showing HCV genome known in the art.

HCV has a positive sense RNA genome of about 9600 nucleoside bases. FIG. 1 is a schematic diagram of approximately 9.5 kb HCV RNA. As shown in FIG. 1, at the 5' and 3' ends of the RNA are the 5' UTR and 3' UTR regions, respectively. Moving forward from the 5' UTR region to the 3' UTR region, located are sequences that encode active structural, core (C), envelope (E1 and E2) and P7 proteins, and non-structural, NS2, NS3, NS4a, NS4b, NS5a and NS5b proteins. The 3' end of the RNA comprises either a poly(A) or poly(U) tail, depending on the type of HCV. The 5' UTR and 3' UTR regions are not translated into proteins but are important to translation and replication of the viral RNA. In particular, the 5' UTR has a ribosome binding site (IRES—Internal Ribosomal Entry Site) that starts the translation of a 3000 amino acid containing protein that is later cut by cellular and viral proteases into active structural (core (C), envelope (E1 and E2) and P7 proteins) and non-structural smaller proteins, including NS2, NS3, NS4a, NS4b, NS5a and NS5b proteins. The HCV nonstructural (NS) proteins are believed to provide the essential catalytic machinery for viral replication. The NS proteins are derived by proteolytic cleavage of the polyprotein. The HCV NS protein 3 (NS3) contains a serine protease activity that helps process the majority of the viral enzymes, and is thus considered essential for viral replication and infectivity. The first 181 amino acids of NS3 (residues 1027-1207 of the viral polyprotein) have been shown to contain the serine protease domain of NS3 that processes all four downstream sites of the HCV polyprotein. The HCV NS3 serine protease and its associated cofactor, NS4A, help process all of the viral enzymes. The 5' UTR is the most highly conserved part of the HCV genome, whereas the sequence of the two envelope proteins (E1 and E2) is highly variable among different HCV isolates.

Typically, the genetic heterogeneity of HCV has been classified by quasispecies and genotype. As used herein, the term "quasispecies" refers to the genetic heterogeneity of the HCV population within an infected individual. As used herein, the terms "genotype" and "subtype" refer to the genomic heterogeneity observed among different HCV isolates. Multiple types and subtypes of HCV have been known in the art, including, e.g., genotypes 1a, 1b, 1c, 2a, 2b, 2c, 3a, 3b, 4a, 5a and 6a (using the classification system of Simmonds et al., 1994, *Hepatology* 19:1321-24; Zein, 2000, *Clin. Microbiol. Rev.* 13:223-235).

As used herein, the term "HCV" includes any types and subtypes of HCV, including genotypes 1a, 1b, 1c, 2a, 2b, 2c, 3a, 3b, 4a, 5a and 6a; and variants thereof. Generally, a "variant" includes a sequence that has one or more changes relative to a reference virus, gene or protein. The origin of the variants includes, for example, gene mutations and polymorphisms. Also, the term "HCV nucleic acid" includes the full-length HCV, and fragments of HCV having partial sequences.

In one aspect, the present invention provides a method of amplifying an HCV nucleic acid obtained from an HCV infected sample by employing RT to prepare a DNA template (cDNA) complementary to a genome of HCV RNA from the sample. A segment of the DNA template is then amplified by employing a two-stage PCR. The DNA template segment includes a target HCV nucleic acid molecule subject to amplification, and amplicons of the target HCV nucleic acid molecule are produced via the two-stage PCR. Each of the RT and PCR processes independently employs one or more primers disclosed herein (for example, SEQ ID NOs. 1-17).

In some embodiments, the amplified target HCV nucleic acid molecule has greater than 8,000 base pairs. In other embodiments, the amplified target HCV nucleic acid molecule has greater than 9,000 base pairs. In yet other embodiments, the amplified target HCV nucleic acid molecule comprises genomes that encode C, E1, E2, NS2, NS3, NS4A, NS4B, NS5A and NS5B proteins. In yet other embodiments, the amplified target HCV nucleic acid molecule has the full-length of nucleotides.

A sample from which a target HCV nucleic acid molecule can be detected is any HCV-infected bodily fluid, cells or cellular debris. Samples from patients, in which the presence of HCV is to be determined, may be, for example, blood, serum, plasma and other body fluids or tissues. An "HCV infected sample" includes HCV RNA in any amount. In some embodiments, the HCV-infected sample is from a HCV positive sample. As used herein, the phrase "HCV positive" sample means that the sample includes HCV RNA in an amount greater than 1000 IU/mL. In some embodiments, the HCV-infected sample includes HCV RNA in an amount less than, or equal to, 1000 IU/mL, for example, in a range of between 10 IU/mL and 1000 IU/mL; between 100 IU/mL and 1000 IU/mL; between 500 IU/mL and 1000 IU/mL; or 700 IU/mL and 1000 IU/mL. In some embodiments, the HCV infected sample from which the target HCV nucleic acid molecule is obtained is an HCV infected patient's plasma.

A "primer" is an oligonucleotide which, upon hybridizing to a template nucleic acid molecule, is capable of acting as a point of synthesis initiation, for example, during an amplification or RT reaction. The length of the primers of the present invention is not critical. Typically, the primer length ranges from 5-150 nucleotides, such as 10-100 nucleotides, 15-80 nucleotides, 15-50 nucleotides, 25-80 nucleotides, 28-80 nucleotides, 20-45 nucleotides, 15-35 nucleotides, or 25-35 nucleotides. For example, additional sequences of 1-100 nucleotides (such as a Tag having 1-50, 1-30, or 1-20 nucleotides) can be added at the 5' end of any one of SEQ ID NOs. 1-17 and variants thereof. In some embodiments, random sequences of 1-100 nucleotides (such as random sequences of 1-50, 1-30, or 1-20 nucleotides) are added at the 5' end of the primers disclosed herein (e.g., oligonucleotides of SEQ ID NOs. 1-14 and variants thereof), but not at their 3' end. In some embodiments, the primers of the invention comprise SEQ ID NOs. 1-17 or variants thereof at their 3' end.

The term "nucleic acid," "nucleotide" and "oligonucleotide" are used interchangeably throughout. Unless noted otherwise, when polynucleotide sequences are presented as a series of one-letter and/or three-letter abbreviations, the sequences are presented in the 5' to 3' direction, in accordance with common practice. The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (U).

In the invention, the RT step is performed using an RT primer, the nucleotide sequence of which comprises SEQ ID NO: 1 or SEQ ID NO: 8:

```
5'-(A)_n-AAAA-3',            (SEQ ID NO: 1)
or

5'-AAAAAAAAAAAAAAAAAAAA-3'.  (SEQ ID NO: 8)
```

The "n" of SEQ ID NO: 1 is typically an integer of 1-26, more typically an integer of 4-20, and even more typically an integer of 10-20.

In some embodiments, the RT primer is a 10-80 mer. In other embodiments, the RT primer is a 15-80 mer. In yet other embodiments, the RT primer is a 15-50 mer. In yet other embodiments, the RT primer is a 15-30 mer. In yet other embodiments, the RT primer is a 18-30 mer.

In some embodiments, the RT primer comprises SEQ ID NO: 1 or SEQ ID NO: 8 at its 3' end.

In some embodiments, the target HCV RNA is primed with an RT primer described above at a 3' untranslated region (3' UTR) of the HCV genome.

Generally, the RT step can be carried out as a separate step. Optionally, it can be carried out in a combined reverse transcription-polymerase chain reaction (RT-PCR). The RT-PCR amplification of RNA is well known in the art and described in, for example, U.S. Pat. Nos. 5,322,770 and 5,310,652; Myers and Gelfand, 1991, *Biochemistry* 30(31):7661-7666; U.S. Pat. No. 5,527,669; Young et al., 1993, *J. Clin. Microbiol.* 31(4):882-886; and Young et al., 1995, *J. Clin. Microbiol.* 33(3):654-657.

During the RT step, in general, HCV RNA comprising the target nucleic acid is isolated from the HCV infected sample in a manner typically performed in a laboratory to prepare an RNA template. In some embodiments, the HCV RNA is isolated from the HCV infected sample using a carrier RNA. Examples of carrier RNAs that can be employed in the invention include poly-A RNA and bacterial tRNA. In certain specific embodiments, bacterial tRNA is employed. A complementary DNA template is prepared from the HCV RNA template using the RT primer and one or more RT enzymes. Any suitable RT condition and RT enzyme, known in the art, can be employed in the invention. Specific examples of RT enzymes that can be employed in the invention include M-MuLV (Moloney Murine Leukemia Virus), such as SuperScript, PrimeScript, PowerScript, Accuscript, ArrayScript and MultiScribe; AMV (Avian Myeloblastosis Virus); and HIV (Human Immunodeficency Virus).

The cDNA template can then be employed for amplification using a two-stage PCR. Generally, the two-stage PCR employs a first stage PCR and a second stage PCR. With the first stage PCR, the HCV cDNA template (or a segment of the HCV cDNA template) that includes the target HCV nucleic acid is amplified by employing a pair of outer primers, i.e., a first outer primer and a second outer primer to produce a first amplification product (amplicons). For example, at least a portion of the amplification product (or a segment of the amplification product) of the first stage PCR is then subsequently further amplified by the second stage PCR employing a pair of inner primers, i.e., a first inner primer and a second inner primer, to produce a second amplification product (amplicons). As in conventional PCR, in each cycle of the amplification reaction any double-stranded nucleic acid molecules in a sample can be rendered single-stranded by denaturation. Hybridization can then take place between the primers and the target nucleic acid molecules.

Typically, the inner or outer primer pair can be the same or different in length. For example, for each of the inner and outer primer pairs, the first primer may be made up of twenty-nine nucleotides; while the second primer can be made up of twenty-two nucleotides. In some embodiments, each of the outer and inner primers independently is a 15-80 mer. In other embodiments, each of the outer and inner primers independently is a 15-50 mer. In yet other embodiments, each of the outer and inner primers independently is a 25-80 mer. In yet other embodiments, each of the outer and inner primers independently is a 28-80 mer. In yet other embodiments, each of the outer and inner primers independently is a 25-50 mer.

In one embodiment, the first inner and outer primers independently are primed at a 5' UTR of the HCV genome, and the second inner and outer primers independently are primed at a NS5B region of the HCV genome. In a specific embodiment, the 5' UTR regions where the first inner and outer primers are primed comprise the regions shown in FIG. 2 for F1 and F2 primers, independently; and the NS5B regions where the second inner and outer primers are primed comprise the regions shown in FIG. 2 for R1 and R2 primers, independently.

In one embodiment, the first outer primer comprises a nucleotide sequence of SEQ ID NO.2:

```
5'-GAGTAGTGTTGGGTCG-3'.      (SEQ ID NO: 2)
```

In another embodiment, the first outer primer comprises a nucleotide sequence as set forth in SEQ ID NO: 9, wherein optionally one, two or three (alternatively one or two) nucleotides at positions 1 through 14 from the 5' end of SEQ ID NO: 9 are independently other nucleotides than those of SEQ ID NO: 9:

```
                                    (SEQ ID NO: 9)
5'-CAAGACTGCTAGCCGAGTAGTGTTGGGTCG-3'.
```

In yet another embodiment, the first outer primer comprises at its 3' end a nucleotide sequence as set froth SEQ ID NO: 9, wherein optionally one, two or three (alternatively one or two) nucleotides thereof independently are other nucleotides than those of SEQ ID NO: 9.

In yet another embodiment, the first outer primer comprises a nucleotide sequence as set froth SEQ ID NO: 9. In yet another embodiment, the first outer primer comprises a nucleotide sequence as set froth SEQ ID NO: 9 at its 3' end.

In one embodiment, the second outer primer comprises a nucleotide sequence as set forth in SEQ ID NO: 3 or SEQ ID NO: 4:

```
5'-CACGCTGTGATAAATG-3';      (SEQ ID NO: 3)

5'-CAVGCTGTGATATATG-3'.      (SEQ ID NO: 4)
```

In another embodiment, the second outer primer comprises a nucleotide sequence as set forth in SEQ ID NO: 10 or 11, wherein optionally one, two or three (alternatively one or two) nucleotides at positions 1 through 12 from the 5' end of SEQ ID NOs: 10 and 11 are independently other nucleotides than those of SEQ ID NOs: 10 and 11:

```
                                  (SEQ ID NO: 10)
5'-CCGGGCAYGAGACACGCTGTGATAAATG-3';

(SEQ ID NO: 11)
5'-TCGGGCACGAGACAVGCTGTGATATATG-3'.
```

In yet another embodiment, the second outer primer comprises at its 3' end a nucleotide sequence as set froth in SEQ ID NO: 10 or 11, wherein optionally one, two or three (alternatively one or two) nucleotides thereof independently are other nucleotides than those of SEQ ID NOs: 10 and 11.

In yet another embodiment, the second outer primer comprises a nucleotide sequence as set froth in SEQ ID NO: 10 or 11. In yet another embodiment, the second outer primer comprises a nucleotide sequence as set froth in SEQ ID NO: 10 or 11 at its 3' end.

In one embodiment, the first inner primer comprises a nucleotide sequence as set forth in SEQ ID NO: 5:

```
5'-GGTGCTTGCGAGTGCC-3'.      (SEQ ID NO: 5)
```

In another embodiment, the first inner primer comprises a nucleotide sequence as set forth in SEQ ID NO: 12, wherein optionally one, two or three (alternatively one or two) nucleotides at positions 1 through 14 from the 5' end of SEQ ID NO: 12 independently are other nucleotides than those of SEQ ID NO: 12:

```
                                    (SEQ ID NO: 12)
5'-GTACTGCCTGATAGGGTGCTTGCGAGTGCC-3'.
```

In yet another embodiment, the first inner primer comprises at its 3' end a nucleotide sequence as set forth in SEQ ID NO: 12, wherein optionally one, two or three (alternatively one or two) nucleotides thereof independently are other nucleotides than those of SEQ ID NO:12.

In yet another embodiment, the first inner primer comprises a nucleotide sequence as set forth in SEQ ID NO: 12. In yet another embodiment, the first inner primer comprises a nucleotide sequence as set forth in SEQ ID NO: 12 at its 3' end.

In yet another embodiment, the first inner primer comprises a nucleotide sequence as set forth in SEQ ID NO: 15, wherein optionally one, two or three (alternatively one or two) nucleotides at positions 1 through 16 from the 5' end of SEQ ID NO: 15 independently are other nucleotides than those of SEQ ID NO: 15:

```
                                    (SEQ ID NO: 15)
5'-AAGTACTGCCTGATAGGGTGCTTGCGAGTGCC-3'.
```

In yet another embodiment, the first inner primer comprises at its 3' end a nucleotide sequence as set forth in SEQ ID NO: 15, wherein optionally one, two or three (alternatively one or two) nucleotides thereof independently are other nucleotides than those of SEQ ID NO:15.

In yet another embodiment, the first inner primer comprises a nucleotide sequence as set forth in SEQ ID NO: 15. In yet another embodiment, the first inner primer comprises a nucleotide sequence as set forth in SEQ ID NO: 15 at its 3' end.

In one embodiment, the second inner primer comprises a nucleotide sequence as set forth in SEQ ID NO: 6 or 7:

```
5'-TAGCCAGCCGTGAACC-3'       (SEQ ID NO: 6)
or

5'-TARCCAGCRACGAACC-3'.      (SEQ ID NO: 7)
```

In another embodiment, the second inner primer comprises a nucleotide sequences as set forth in SEQ ID NO: 13 or 14, wherein optionally one, two or three (alternatively one or two) nucleotides at positions 1 through 12 from the 5' end of SEQ ID NOs: 13 and 14 are independently other nucleotides than those of SEQ ID NOs: 13 and 14:

```
                                     (SEQ ID NO: 13)
5'-TCTCCCCCGCTGTAGCCAGCCGTGAACC-3'
or (SEQ ID NO: 14)
5'-TCTCCCCCGCTGTARCCAGCRACGAACC-3'.
```

In yet another embodiment, the second inner primer comprises at its 3' end a nucleotide sequences as set forth in SEQ ID NO: 13 or 14, wherein optionally one, two or three (alternatively one or two) nucleotides thereof independently are other nucleotides than those of SEQ ID NOs: 13 and 14.

In another embodiment, the second inner primer comprises a nucleotide sequences as set forth in SEQ ID NO: 16 or 17, wherein optionally one, two or three (alternatively one or two) nucleotides at positions 1 through 13 from the 5' end of SEQ ID NOs: 16 and 17 are independently other nucleotides than those of SEQ ID NOs: 16 and 17:

```
                                      (SEQ ID NO: 16)
5'-ATCTCCCCCGCTGTAGCCAGCCGTGAACC-3'
```

-continued or (SEQ ID NO: 17)
5'-ATCTCCCCCGCTGTARCCAGCRACGAACC-3'.

In yet another embodiment, the second inner primer comprises at its 3' end a nucleotide sequences as set forth in SEQ ID NO: 16 or 17, wherein optionally one, two or three (alternatively one or two) nucleotides thereof independently are other nucleotides than those of SEQ ID NOs: 16 and 17.

In yet another embodiment, the second inner primer comprises a nucleotide sequences as set forth in SEQ ID NO: 16 or 17. In yet another embodiment, the second inner primer comprises a nucleotide sequences as set forth in SEQ ID NO: 16 or 17 at its 3' end.

In a first specific embodiment, the first outer primer comprises a nucleotide sequence as set forth in SEQ ID NO: 9, wherein optionally one, two or three (alternatively one or two) nucleotides at positions 1 through 14 from the 5' end of SEQ ID NO:9 are independently other nucleotides than those of SEQ ID NO:9; and the second outer primer comprises a nucleotide sequence set forth in SEQ ID NO: 10 or 11, wherein optionally one, two or three (alternatively one or two) nucleotides at positions 1 through 12 from the 5' end of SEQ ID NOs: 10 and 11 are independently other nucleotides than those of SEQ ID NOs: 10 and 11.

In a second specific embodiment, the first inner primer comprises a nucleotide sequence as set forth in SEQ ID NO: 12, wherein optionally one, two or three (alternatively one or two) nucleotides at positions 1 through 14 from the 5' end of SEQ ID NO:12 are independently other nucleotides than those of SEQ ID NO:12; and the second inner primer comprises a nucleotide sequence set forth in SEQ ID NO: 13 or 14, wherein optionally one, two or three (alternatively one or two) nucleotides at positions 1 through 12 from the 5' end of SEQ ID NOs: 13 and 14 are independently other nucleotides than those of SEQ ID NOs: 13 and 14.

In a third specific embodiment, the first outer primer comprises a nucleotide sequence as set forth in SEQ ID NO: 9, wherein optionally one, two or three (alternatively one or two) nucleotides at positions 1 through 14 from the 5' end of SEQ ID NO:9 are independently other nucleotides than those of SEQ ID NO:9; the second outer primer comprises a nucleotide sequence set forth in SEQ ID NO: 10 or 11, wherein optionally one, two or three (alternatively one or two) nucleotides at positions 1 through 12 from the 5' end of SEQ ID NOs: 10 and 11 are independently other nucleotides than those of SEQ ID NOs: 10 and 11; the first inner primer comprises a nucleotide sequence as set forth in SEQ ID NO: 12, wherein optionally one, two or three (alternatively one or two) nucleotides at positions 1 through 14 from the 5' end of SEQ ID NO:12 are independently other nucleotides than those of SEQ ID NO:12; and the second inner primer comprises a nucleotide sequence set forth in SEQ ID NO: 13 or 14, wherein optionally one, two or three (alternatively one or two) nucleotides at positions 1 through 12 from the 5' end of SEQ ID NOs: 13 and 14 are independently other nucleotides than those of SEQ ID NOs: 13 and 14. In one aspect of this embodiment, the target HCV nucleic acid molecule has greater than 8,000 base pairs. In another aspect of this embodiment, the target HCV nucleic acid molecule is genotype 1a or 1b. In yet another aspect of this embodiment, the target HCV nucleic acid molecule is genotype 1a or 1b having greater than 8,000 base pairs.

In a fourth specific embodiment, the first outer primer comprises a nucleotide sequence as set forth in SEQ ID NO: 9 at its 3' end, wherein optionally one, two or three (alternatively one or two) nucleotides are independently other nucleotides than those of SEQ ID NO:9; the second outer primer comprises a nucleotide sequence set forth in SEQ ID NO: 10 or 11 at its 3' end, wherein optionally one, two or three (alternatively one or two) nucleotides are independently other nucleotides than those of SEQ ID NOs: 10 and 11; the first inner primer comprises a nucleotide sequence as set forth in SEQ ID NO: 12 at its 3' end, wherein optionally one, two or three (alternatively one or two) nucleotides are independently other nucleotides than those of SEQ ID NO:12; and the second inner primer comprises a nucleotide sequence set forth in SEQ ID NO: 13 or 14 at its 3' end, wherein optionally one, two or three (alternatively one or two) nucleotides are independently other nucleotides than those of SEQ ID NOs: 13 and 14. In one aspect of this embodiment, the target HCV nucleic acid molecule has greater than 8,000 base pairs. In another aspect of this embodiment, the target HCV nucleic acid molecule is genotype 1a or 1b. In yet another aspect of this embodiment, the target HCV nucleic acid molecule is genotype 1a or 1b having greater than 8,000 base pairs.

In a fifth specific embodiment, the target HCV nucleic acid molecule is genotype 1a having greater than 8,000 base pairs. In one aspect of this embodiment, the outer primer comprises a nucleotide sequence as set forth in SEQ ID NO: 9, wherein optionally one, two or three (alternatively one or two) nucleotides at positions 1 through 14 from the 5' end of SEQ ID NO:9 are independently other nucleotides than those of SEQ ID NO:9; the second outer primer comprises a nucleotide sequence set forth in SEQ ID NO: 10, wherein optionally one, two or three (alternatively one or two) nucleotides at positions 1 through 12 from the 5' end of SEQ ID NO: 10 are independently other nucleotides than those of SEQ ID NO: 10; the first inner primer comprises a nucleotide sequence as set forth in SEQ ID NO: 12, wherein optionally one, two or three (alternatively one or two) nucleotides at positions 1 through 14 from the 5' end of SEQ ID NO:12 are independently other nucleotides than those of SEQ ID NO:12; and the second inner primer comprises a nucleotide sequence set forth in SEQ ID NO: 13, wherein optionally one, two or three (alternatively one or two) nucleotides at positions 1 through 12 from the 5' end of SEQ ID NO: 13 are independently other nucleotides than those of SEQ ID NO: 13. In another aspect of this embodiment, the outer primer comprises a nucleotide sequence as set forth in SEQ ID NO: 9 at its 3' end, wherein optionally one, two or three (alternatively one or two) nucleotides are independently other nucleotides than those of SEQ ID NO:9; the second outer primer comprises a nucleotide sequence set forth in SEQ ID NO: 10 at its 3' end, wherein optionally one, two or three (alternatively one or two) nucleotides are independently other nucleotides than those of SEQ ID NO: 10; the first inner primer comprises a nucleotide sequence as set forth in SEQ ID NO: 12 at its 3' end, wherein optionally one, two or three (alternatively one or two) nucleotides are independently other nucleotides than those of SEQ ID NO:12; and the second inner primer comprises a nucleotide sequence set forth in SEQ ID NO: 13 at its 3' end, wherein optionally one, two or three (alternatively one or two) nucleotides are independently other nucleotides than those of SEQ ID NO: 13. In yet another aspect of this embodiment, the first outer primer comprises a nucleotide sequence as set forth in SEQ ID NO: 9; the second outer primer comprises a nucleotide sequence set forth in SEQ ID NO: 10; the first inner primer comprises a nucleotide sequence as set forth in SEQ ID NO: 12; and the second inner primer comprises a nucleotide sequence set forth in SEQ ID NO: 13. In yet another aspect of this embodiment, the first outer primer comprises a nucleotide sequence as set forth in SEQ ID NO:

9 at its 3' end; the second outer primer comprises a nucleotide sequence set forth in SEQ ID NO: 10 at its 3' end; the first inner primer comprises a nucleotide sequence as set forth in SEQ ID NO: 12 at its 3' end; and the second inner primer comprises a nucleotide sequence set forth in SEQ ID NO: 13 at its 3' end.

In a sixth specific embodiment, the target HCV nucleic acid molecule is genotype 1b having greater than 8,000 base pairs. In one aspect of this embodiment, the first outer primer comprises a nucleotide sequence as set forth in SEQ ID NO: 9, wherein optionally one, two or three (alternatively one or two) nucleotides at positions 1 through 14 from the 5' end of SEQ ID NO:9 are independently other nucleotides than those of SEQ ID NO:9; the second outer primer comprises a nucleotide sequence set forth in SEQ ID NO: 11, wherein optionally one, two or three (alternatively one or two) nucleotides at positions 1 through 12 from the 5' end of SEQ ID NO: 11 are independently other nucleotides than those of SEQ ID NO: 11; the first inner primer comprises a nucleotide sequence as set forth in SEQ ID NO: 12, wherein optionally one, two or three (alternatively one or two) nucleotides at positions 1 through 14 from the 5' end of SEQ ID NO:12 are independently other nucleotides than those of SEQ ID NO:12; and the second inner primer comprises a nucleotide sequence set forth in SEQ ID NO: 14, wherein optionally one, two or three (alternatively one or two) nucleotides at positions 1 through 12 from the 5' end of SEQ ID NO: 14 are independently other nucleotides than those of SEQ ID NO: 14. In another aspect of this embodiment, the first outer primer comprises a nucleotide sequence as set forth in SEQ ID NO: 9 at its 3' end, wherein optionally one, two or three (alternatively one or two) nucleotides are independently other nucleotides than those of SEQ ID NO:9; the second outer primer comprises a nucleotide sequence set forth in SEQ ID NO: 11 at its 3' end, wherein optionally one, two or three (alternatively one or two) nucleotides are independently other nucleotides than those of SEQ ID NO: 11; the first inner primer comprises a nucleotide sequence as set forth in SEQ ID NO: 12 at its 3' end, wherein optionally one, two or three (alternatively one or two) nucleotides are independently other nucleotides than those of SEQ ID NO:12; and the second inner primer comprises a nucleotide sequence set forth in SEQ ID NO: 14 at its 3' end, wherein optionally one, two or three (alternatively one or two) nucleotides are independently other nucleotides than those of SEQ ID NO: 14. In yet another aspect of this embodiment, the first outer primer comprises a nucleotide sequence as set forth in SEQ ID NO: 9; the second outer primer comprises a nucleotide sequence set forth in SEQ ID NO: 11; the first inner primer comprises a nucleotide sequence as set forth in SEQ ID NO: 12; and the second inner primer comprises a nucleotide sequence set forth in SEQ ID NO: 14. In yet another aspect of this embodiment, the first outer primer comprises a nucleotide sequence as set forth in SEQ ID NO: 9 at its 3' end; the second outer primer comprises a nucleotide sequence set forth in SEQ ID NO: 11 at its 3' end; the first inner primer comprises a nucleotide sequence as set forth in SEQ ID NO: 12 at its 3' end; and the second inner primer comprises a nucleotide sequence set forth in SEQ ID NO: 14 at its 3' end.

In some specific embodiments, the first and second outer primers are as described above in each of the first through fourth specific embodiments; and the first inner primer comprises a nucleotide sequence as set forth in SEQ ID NO: 15, wherein optionally one, two or three (alternatively one or two) nucleotides are independently other nucleotides than those of SEQ ID NO:15; and the second inner primer comprises a nucleotide sequence as set forth in SEQ ID. NO. 16 or 17, wherein optionally one, two or three (alternatively one or two) nucleotides are independently other nucleotides than those of SEQ ID NOs:16 and 17. In some more specific embodiments, the nucleotide(s) that are optionally different from those of SEQ ID NO:15 are independently at positions 1 through 16 from the 5' end of SEQ ID NO:15; and the nucleotide(s) that are optionally different from those of SEQ ID NOs:16 and 17 are independently at positions 1 through 13 from the 5' end of SEQ ID. NOs. 16 and 17. In some more specific embodiments, the first inner primer comprises a nucleotide sequence as set forth in SEQ ID NO: 15; and the second inner primer comprises a nucleotide sequence as set forth in SEQ ID. NO. 16 or 17.

In some specific embodiments, the target HCV nucleic acid molecule is genotype 1a having greater than 8,000 base pairs; the first and second outer primers are as described above in the fifth specific embodiment; and the first inner primer comprises a nucleotide sequence as set forth in SEQ ID NO: 15, wherein optionally one, two or three (alternatively one or two) nucleotides are independently other nucleotides than those of SEQ ID NO:15; and the second inner primer comprises a nucleotide sequence as set forth in SEQ ID. NO. 16, wherein optionally one, two or three (alternatively one or two) nucleotides are independently other nucleotides than those of SEQ ID NO:16. In some more specific embodiments, the nucleotide(s) that are optionally different from those of SEQ ID NO:15 are independently at positions 1 through 16 from the 5' end of SEQ ID NO:15; and the nucleotide(s) that are optionally different from those of SEQ ID NO:16 are independently at positions 1 through 13 from the 5' end of SEQ ID. NO. 16. In some more specific embodiments, the first inner primer comprises a nucleotide sequence as set forth in SEQ ID NO: 15; and the second inner primer comprises a nucleotide sequence as set forth in SEQ ID. NO. 16.

In some specific embodiments, the target HCV nucleic acid molecule is genotype 1b having greater than 8,000 base pairs; the first and second outer primers are as described above in the fifth specific embodiment; and the first inner primer comprises a nucleotide sequence as set forth in SEQ ID NO: 15, wherein optionally one, two or three (alternatively one or two) nucleotides are independently other nucleotides than those of SEQ ID NO:15; and the second inner primer comprises a nucleotide sequence as set forth in SEQ ID. NO. 17, wherein optionally one, two or three (alternatively one or two) nucleotides are independently other nucleotides than those of SEQ ID NO:17. In some more specific embodiments, the nucleotide(s) that are optionally different from those of SEQ ID NO:15 are independently at positions 1 through 16 from the 5' end of SEQ ID NO:15; and the nucleotide(s) that are optionally different from those of SEQ ID NO:17 are independently at positions 1 through 13 from the 5' end of SEQ ID. NO. 17. In some more specific embodiments, the first inner primer comprises a nucleotide sequence as set forth in SEQ ID NO: 15; and the second inner primer comprises a nucleotide sequence as set forth in SEQ ID. NO. 17.

Any suitable PCR condition known in the art can be employed in the invention. For example, a number of guidance can be found in the art, e.g., Sambrook et al., 1989, Molecular Cloning—A Laboratory Manual, Cold Spring Harbor Laboratory, Cold Spring Harbor, N.Y.; Wetmur, 1991, *Critical Reviews in Biochem. and Mol. Biol.* 26(¾):227-259; Ausubel et al. (eds.), 1995, *Current Protocols in Molecular Biology*, (John Wiley & Sons, Inc., New York) at Unit 2.10; and U.S. Pat. No. 5,789,550. Also, such guidance can be found in PCR protocols published by PCR reagent makers and/or vendors, such as Perkin Elmer (Norwalk, Conn.). Specifically, suitable PCR conditions can be determined considering, for example, a number of variables including the length and base pair concentration of the oligonucleotides, ionic strength, the incidence of mismatched base pairs, and the temperature chosen for oligonucleotide annealing, following the guidance provided in the art.

Generally, a PCR amplification reaction mixture that includes the DNA template contains reagents necessary to carry out an amplification reaction. Typically, the mixture contains an agent for polymerization, such as thermostable DNA polymerase. More typically, in addition to thermostable DNA polymerase, the mixture deoxynucleoside 5' triphosphates (dNTP's), and a divalent metal cation in a suitable buffer. Typical examples of thermostable DNA polymerases that can be employed in the invention include Taq DNA polymerase, Klentaq DNA polymerase, Pfu DNA polymerase, Tth DNA polymerase, Pwo DNA polymerase, Pfx DNA polymerase and Tfl DNA polymerase.

In one specific embodiment, Klentaq and Pfu DNA polymerases are employed in the invention. In another specific embodiment, Klentaq and Pfu DNA polymerases are employed in the invention in a ratio of Klentaq DNA polymerase:Pfu DNA polymerase between 1:1 and 3:1. It is noted that the ranges described herein with reference to "between" two end points also include the end points. In yet another specific embodiment of the invention, the PCR reaction mixture of the first stage PCR comprises between 2 units and 3 units of Klentaq DNA polymerase, and between 1 unit and 1.5 units of Pfu DNA polymerase. In yet another specific embodiment of the invention, the PCR reaction mixture of the second stage PCR comprises between 2.5 units and 3.5 units of Klentaq DNA polymerase, and between 1 unit and 2 units of Pfu DNA polymerase.

In yet another specific embodiment of the invention, betaine is employed in each of the first and second PCR stages independently. In yet another specific embodiment of the invention, the PCR reaction mixture for each of the first and second PCR stages independently comprises betaine in an amount of between 0.75 M and 2 M.

In one embodiment, during each of the first and second stage PCRs, each PCR reaction mixture independently is incubated at temperature T1 for time period R1, and subsequently followed by a plurality of touchdown PCR cycles. Each touchdown cycle comprises incubation of the PCR reaction mixture at temperature T2 for time period R2, subsequently at a temperature of [T3−(V ° C.×m)] for $m^{th}$ cycle for time period R3, and subsequently at temperature T4 for time period R4. Typically, T1 and T2 independently are in a range of between 90° C. and 100° C.; T3 and T4 independently are in a range of between 65° C. and 70° C.; R1 is in a range of between 1 minute and 5 minutes; R2 is in a range of 5 seconds and 45 seconds; R3 is in a range of between 10 seconds and 40 seconds; R4 is in a range of between 5 minutes and 20 minutes; and V is in a range of between 0.2° C. and 0.8° C. (e.g., 0.5° C.). More typically, R1 is in a range of between 1 minute and 3 minutes; R2 is in a range of 10 seconds and 20 seconds; R3 is in a range of between 15 seconds and 25 seconds; and R4 is in a range of between 8 minutes and 15 minutes. In a specific embodiment, R1 is in a range of between 1 minute and 3 minutes; R2 is in a range of 10 seconds and 20 seconds; R3 is in a range of between 15 seconds and 25 seconds; R4 is in a range of between 8 minutes and 15 minutes; T1 is 94° C.; T2 is 94° C.; T3 is 68° C.; T4 is 68° C.; V is 0.5° C.

Typically, the number of the touchdown PCR cycles is in a range of between 20 and 50, such as between 20 and 40. In a specific embodiment, the number of the touchdown PCR cycles is 30.

As described above, typically, the RT and PCR steps can be carried out in a combined reverse transcription-polymerase chain reaction (RT-PCR). In some specific embodiments, the RT and PCR steps are combined in a reverse transcription-polymerase chain reaction (RT-PCR), preferably nested RT-PCR.

In another aspect, the present invention provides methods of assaying an HCV nucleic acid molecule in an HCV infected sample. In the assay methods, the amplified HCV nucleic acid molecule prepared by an amplification method described above is the sequenced by any suitable method known in the art. The determined sequence of the HCV nucleic acid molecule can be useful for, for example, developing new approaches for diagnosing and/or treating HCV infection in patients.

In yet another aspect, the present invention provides kits for amplifying and/or assaying an HCV nucleic acid molecule from an HCV infected sample. Typically, the kits of the invention comprise an RT primer described above; a pair of outer PCR primers (a first outer primer and a second outer primer) described above; and a pair of inner PCR primers (a first outer primer and a second outer primer) described above. In some embodiments, the kits of the invention further include a reverse transcriptase and a DNA polymerase. Specific examples of such RT and PCR primers, reverse transcriptases, and DNA polymerases are as described above. The kits can further comprise written instructions describing how to use the kits (e.g., instructions describing methods for HCV amplification and/or assaying) and chemical reagents required for the method, as well as any other components. These kits can further comprise, for example, reagents for sample collection (e.g., the collection of a blood sample) and reagents for the collection and purification of HCV RNA from a HCV infected sample.

The present invention also provides PCR primers. In one embodiment, a primer of the invention comprises a nucleotide sequence as set forth in SEQ ID NO: 9, wherein optionally one, two or three (alternatively one or two) nucleotides at positions 1 through 14 from the 5' end of SEQ ID NO:9 are independently other nucleotides than those of SEQ ID NO:9; a nucleotide sequence set forth in SEQ ID NO: 10, wherein optionally one, two or three (alternatively one or two) nucleotides at positions 1 through 12 from the 5' end of SEQ ID NO: 10 are independently other nucleotides than those of SEQ ID NO: 10; a nucleotide sequence set forth in SEQ ID NO: 11, wherein optionally one, two or three (alternatively one or two) nucleotides at positions 1 through 12 from the 5' end of SEQ ID NO: 11 are independently other nucleotides than those of SEQ ID NO: 11; a nucleotide sequence as set forth in SEQ ID NO: 12, wherein optionally one, two or three (alternatively one or two) nucleotides at positions 1 through 14 from the 5' end of SEQ ID NO:12 are independently other nucleotides than those of SEQ ID NO:12; a nucleotide sequence set forth in SEQ ID NO: 13, wherein optionally one, two or three (alternatively one or two) nucleotides at positions 1 through 12 from the 5' end of SEQ ID NO: 13 are independently other nucleotides than those of SEQ ID NO: 13; a nucleotide sequence set forth in SEQ ID NO: 14, wherein optionally one, two or three (alternatively one or two) nucleotides at positions 1 through 12 from the 5' end of SEQ ID NO: 14 are independently other nucleotides than those of SEQ ID NO: 14; a nucleotide sequence set forth in SEQ ID NO: 15, wherein optionally one, two or three (alternatively one or two) nucleotides at positions 1 through 16 from the 5' end of SEQ ID NO: 15 are independently other nucleotides than those of SEQ ID NO: 15; a nucleotide sequence set forth in SEQ ID NO: 16, wherein optionally one, two or three (alternatively one or two) nucleotides at positions 1 through 13 from the 5' end of SEQ ID NO: 16 are independently other nucleotides than those of SEQ ID NO: 16; or a nucleotide sequence set forth in SEQ ID NO: 17, wherein optionally one, two or three (alternatively one or two) nucleotides at positions 1 through 13 from the 5' end of SEQ ID NO: 17 are independently other nucleotides than those of SEQ ID NO: 17. In another embodiment, a primer of the invention comprises a nucleotide sequence as set forth in SEQ ID NO: 9 at its 3' end, wherein optionally one, two or three (alternatively one or two) nucleotides are independently other nucleotides than those of SEQ ID NO:9; a nucleotide sequence set forth in SEQ ID NO: 10 at its 3' end, wherein optionally one, two or three (alternatively one or two) nucleotides are independently other nucleotides than those of SEQ ID NO: 10; a nucleotide sequence set forth in SEQ ID NO: 11 at its 3' end, wherein optionally one, two or three (alternatively one or two) nucleotides are independently other nucleotides than those of SEQ ID NO: 11; a nucleotide sequence as set forth in SEQ ID NO: 12 at its 3' end, wherein optionally one, two or three (alternatively one or two) nucleotides are independently other nucleotides than those of SEQ ID NO:12; a nucleotide sequence set forth in SEQ ID NO: 13, wherein optionally one, two or three (alternatively one or two) nucleotides are independently other nucleotides than those of SEQ ID NO: 13; or a nucleotide sequence set forth in SEQ ID NO: 14 at its 3' end, wherein optionally one, two or three (alternatively one or two) nucleotides are independently other nucleotides than those of SEQ ID NO: 14. In yet another embodiment, a primer of the invention comprises a nucleotide sequence as set forth in SEQ ID NO: 9; a nucleotide sequence set forth in SEQ ID NO: 10; a nucleotide sequence set forth in SEQ ID NO: 11; a nucleotide sequence as set forth in SEQ ID NO: 12; a nucleotide sequence set forth in SEQ ID NO: 13; a nucleotide sequence set forth in SEQ ID NO: 14; a nucleotide sequence set forth in SEQ ID NO: 15, wherein optionally one, two or three (alternatively one or two) nucleotides of SEQ ID NO: 15 are independently other nucleotides than those of SEQ ID NO: 15; a nucleotide sequence set forth in SEQ ID NO: 16, wherein optionally one, two or three (alternatively one or two) nucleotides of SEQ ID NO: 16 are independently other nucleotides than those of SEQ ID NO: 16; or a nucleotide sequence set forth in SEQ ID NO: 17, wherein optionally one, two or three (alternatively one or two) nucleotides of SEQ ID NO: 17 are independently other nucleotides than those of SEQ ID NO: 17. In yet another embodiment, a primer of the invention comprises a nucleotide sequence as set forth in SEQ ID NO: 9 at its 3' end; a nucleotide sequence as set forth in SEQ ID NO: 10 at its 3' end; a nucleotide sequence as set forth in SEQ ID NO: 11 at its 3' end; a nucleotide sequence as set forth in SEQ ID NO: 12 at its 3' end; a nucleotide sequence as set forth in SEQ ID NO: 13 at its 3' end; a nucleotide sequence as set forth in SEQ ID NO: 14 at its 3' end. In yet another embodiment, a primer of the invention comprises a nucleotide sequence as set forth in SEQ ID NO: 15 at its 3' end; a nucleotide sequence set forth in SEQ ID NO: 16 at its 3' end; or a nucleotide sequence set forth in SEQ ID NO: 17 at its 3' end. Any combinations of these primers are also encompassed by the present invention. Specific lengths of the primers of the invention are as described above for the amplification methods of the invention.

The present invention also provides kits for assaying an HCV nucleic acid. In one embodiment, a kit of the invention comprises a PCR primer of the invention described in above. In one specific embodiment, the kit comprises a pair of the outer PCR primers described above. In another specific embodiment, the kit comprises a pair of the inner PCR primers. In yet another embodiment, a kit of the invention comprises a PCR primer of the invention and an RT primer described above. Specific examples of the RT and PCR primers included in the kits are as described above.

In some embodiments, each of the PCR primer(s) employed in the methods and kits of the invention comprises a nucleotide sequence at least 80%, 85%, 89% or 90% identical to SEQ ID Nos. 2-7 and 9-17, respectively.

The sequence of the population of PCR amplicons obtained via the RT-PCR methods described above can be sequenced directly. Alternatively, the PCR amplicons from the population of amplified DNA can be molecularly cloned (or subcloned), and the cloned (or subcloned) products can then be used for nucleotide sequence determination.

In one embodiment, the amplicons prepared by the RT-PCR methods described above are cloned (or subcloned). Such cloning can be done by any suitable method known in the art. The inner PCR primers could be modified to allow complementarities to restriction endonuclease sites, allowing the product to be ligated into a vector digested with the appropriate restriction endonuclease. Alternatively, blunt end cloning can be utilized to directly insert a PCR amplicon into a non-product specific vector sequence. Since DNA polymerases commonly utilized in PCR may polymerize an additional deoxyadenosine at the 3' end of a PCR amplicon, TA cloning can be used to subclone an amplicon as well. The efficiency of this non-specific addition of deoxyadensine to the 3' end of PCR amplicons can be modulated by modifying sequence at the 5' end of PCR primers, such that a 5' terminal deoxyadenosine residue increases the fraction of PCR amplicons possessing a 3' dexyadenosine overhang, thereby improving efficiency of TA cloning (see Peng et al., Adenosine added on the primer 5' end improved TA cloning efficiency of polymerase chain reaction products, *Analytical Biochemistry*, Volume 363, Issue 1, 1 Apr. 2007, Pages 163-165).

In one specific embodiment, the cloned products are prepared from the amplicons prepared by the RT-PCR methods described above, wherein and the first inner primer comprises a nucleotide sequence as set forth in SEQ ID NO: 15, and the second inner primer comprises a nucleotide sequence as set forth in SEQ ID NO: 16 or 17. In another specific embodiment, the first inner primer comprises a nucleotide sequence as set forth in SEQ ID NO: 15, wherein optionally one, two or three nucleotides of SEQ ID NO: 15 independently are other nucleotides than those of SEQ ID NO: 15; and the second inner primer comprises a nucleotide sequence as set forth in SEQ ID NO: 16 or 17, wherein optionally one, two or three nucleotides of SEQ ID NO: 16 and SEQ ID NO: 17 are independently other nucleotides than those of SEQ ID NO: 16 and SEQ ID NO: 17. In yet another specific embodiment, the first inner primer comprises a nucleotide sequence as set forth in SEQ ID NO: 15, wherein optionally one, two or three nucleotides at positions 1 through 16 from the 5' end of SEQ ID NO: 15 independently are other nucleotides than those of SEQ ID NO: 15; and the second inner primer comprises a nucleotide sequence as set forth in SEQ ID NO: 16 or 17, wherein optionally one, two or three nucleotides at positions 1 through 13 from the 5' end of SEQ ID NO: 16 and SEQ ID NO: 17 are independently other nucleotides than those of SEQ ID NO: 16 and SEQ ID NO: 17.

The cloned (or subcloned) products can then be used in multiple downstream applications, including nucleotide sequence determination. For example, the cloned products can be used for transfecting a host organism, and plasmids from the host organism can be amplified in vivo, allowing sequence analysis of individual viral variants. Cloned amplicons or fragments thereof can also be cloned into other vectors. Numerous methods can be employed to introduce amplicons into an appropriate vector (see, for example, Sambrook et al., 1989, *Molecular Cloning—A Laboratory Manual*, Cold Spring Harbor Laboratory, Cold Spring Harbor, N.Y.; Wetmur, 1991, *Current Protocols in Molecular Biology*, (John Wiley & Sons, Inc., New York):

The primers can be natural or synthetic. For PCR, the primers are preferably single-stranded oligodeoxyribonucleotides. Typically, the primers disclosed herein can be synthesized by any suitable method known in the art, e.g. Ozaki et al, *Nuc. Acids Res.* 20: 5205-5214 (1992); Agrawal et al, *Nuc. Acids Res.* 18: 5419-5423 (1990) or the like. Conveniently, the oligonucleotide primers are synthesized on an automated DNA synthesizer, e.g. an Applied Biosystems, Inc, Foster City, Calif. model 392, 394, or 3900 DNA/RNA synthesizer using standard chemistries such as phosphoramidite chemistry (Beaucage and Iyer, *Tetrahedron* 48: 2223-2311 (1992), U.S. Pat. Nos. 4,980,460, 4,725,677, 4,415,732, 4,458,066 and 4,973,679), or are obtained from commercial vendors (Invitrogen, Carlsbad, Calif. USA).

All cited documents are incorporated herein by reference.

In order that this invention is more fully understood, the following preparative and testing examples are set forth. These examples are for the purpose of illustration only and are not to be construed as limiting the scope of the invention in any way.

EXEMPLIFICATION

1. Methods and Material:

Extraction of RNA from Plasma

Extraction of RNA, including HCV viral RNA, from plasma was carried out with the QIAamp Virus BioRobot 9604 Kit (Qiagen, Valencia, Calif. USA), except that the manufacturer's instructions were modified for manually isolation. Briefly, plasma (220~660 µl) was mixed with Protease (40~120 µl) and QIAamp AL buffer (240~720 µl) supplemented with 20 µg of carrier RNA per column. The mixture was incubated for 15 min at 56° C. Absolute ethanol (293~875 µl) was added to each well and mixed well. The mixture was loaded into QIAamp column and passed through the column by suction with a peristaltic micropump (IPS-16; Ismatec, Zurich, Switzerland). The column was washed with 1000 µl of AW1 buffer and 1000 µl of AW2 buffer (Qiagen), respectively, by applying vacuum as described above. The column was washed with 1000 µl AW2 buffer by spinning at 6,000×g for 10 min and then dried by spinning at 6,000×g for 15 min. 40 µl of RNA storage solution (Ambion) was loaded into each column and incubated at RT for 5 min. The RNA was eluted by centrifugation at 6,000×g for 10 min. The elution was repeated once to increase the yield. The isolated RNA was preferably used immediately or stored at −80° C. Up to 96 specimens could be processed from one QIAamp 96 plate and multiple plates can be used to increase throughput.

Amplification and Sequencing of the HCV Polyprotein Coding Region from Patient Plasma Sequence analysis of HCV was done by nested reverse-transcriptase polymerase chain reaction (RT-PCR) amplification of an approximately 8991 nucleotide HCV RNA fragment (residues 286 to 9277, HCV reference sequence H77, NCBI accession NC_004102), spanning the HCV polyprotein coding region. A complementary DNA (cDNA) fragment spanning the HCV polyprotein coding region was synthesized from viral RNA, primed with 2.5 mM oligo-dA$_{20}$, using a modified Superscript III RNase H-Reverse Transcriptase kit (Invitrogen, CA); modifications include using 400 units of Superscript III, 40 units of RNAseOUT (Invitrogen), PC2 reaction buffer (50 mM Tris-HCl pH 9.1, 16 mM ammonium sulfate, 3.5 mM magnesium chloride, and 150 mg/ml BSA; AB Peptides, MO), and ramping extension temperatures (25° C. for 10 min, 42° C. for 60 min, 50° C. for 30 min, and 55° C. for 30 min) in the RT reaction. The completed RT reaction was diluted 1:1 into the first PCR reaction (40 µl), containing PC2 reaction buffer, 200 mM dNTPs (Clontech, CA), 1.5 M betaine (Sigma Aldrich, MO), 2.56 units Klentaq DNA polymerase (AB Peptides, MO), 1.28 units Pfu DNA polymerase (Stratagene, CA), and 400 mM each primer:

TABLE 1

List of primers used for the amplification of HCV coding region

| | | |
|---|---|---|
| RT primer | Oligo d(A) (SEQ ID NO: 8) | 5'-AAAAAAAAAAAAAAAAAAAA-3' |
| Genotype 1a PCR1 | GEN1.F1: (SEQ ID NO: 9) | 5'-CAAGACTGCTAGCCGAGTAGTGTT GGGTCG-3' |
| | GEN1A.R1 (SEQ ID NO: 10) | 5'-CCGGGCAYGAGACACGCTGTGATA AATG-3' |
| Genotype 1a PCR2 | GEN1.F2 (SEQ ID NO: 12) | 5'-GTACTGCCTGATAGGGTGCTTGCG AGTGCC-3' |
| | GEN1A.R2 (SEQ ID NO: 13) | 5'-TCTCCCCCGCTGTAGCCAGCCGTG AACC-3' |
| Genotype 1b PCR1 | GEN1.F1 (SEQ ID NO: 9) | 5'-CAAGACTGCTAGCCGAGTAGTGTT GGGTCG-3' |
| | GEN1B.R1 (SEQ ID NO: 11) | 5'-TCGGGCACGAGACAVGCTGTGATA TATG-3' |
| Genotype 1b PCR2 | GEN1.F2 (SEQ ID NO: 12) | 5'-GTACTGCCTGATAGGGTGCTTGCG AGTGCC-3' |
| | GEN1B.R2 (SEQ ID NO: 14) | 5'-TCTCCCCCGCTGTARCCAGCRACG AACC |
| Genotype 1a/1b; PCR2 TA cloning | GEN1.C1.F2 (SEQ ID NO: 15) | 5'-AAGTACTGCCTGATAGGGTGCTTG CGAGTGCC-3' |
| Genotpye 1a PCR 2 TA Cloning | GEN1A.C1.R2 (SEQ ID NO: 16) | 5'-ATCTCCCCCGCTGTAGCCAGCCGT GAACC-3' |
| Genotype 1b PCR2 TA Cloning | GEN1B.C1.R2 (SEQ ID NO: 17) | 5'-ATCTCCCCCGCTGTARCCAGCRAC GAACC-3' |

Figure 2:
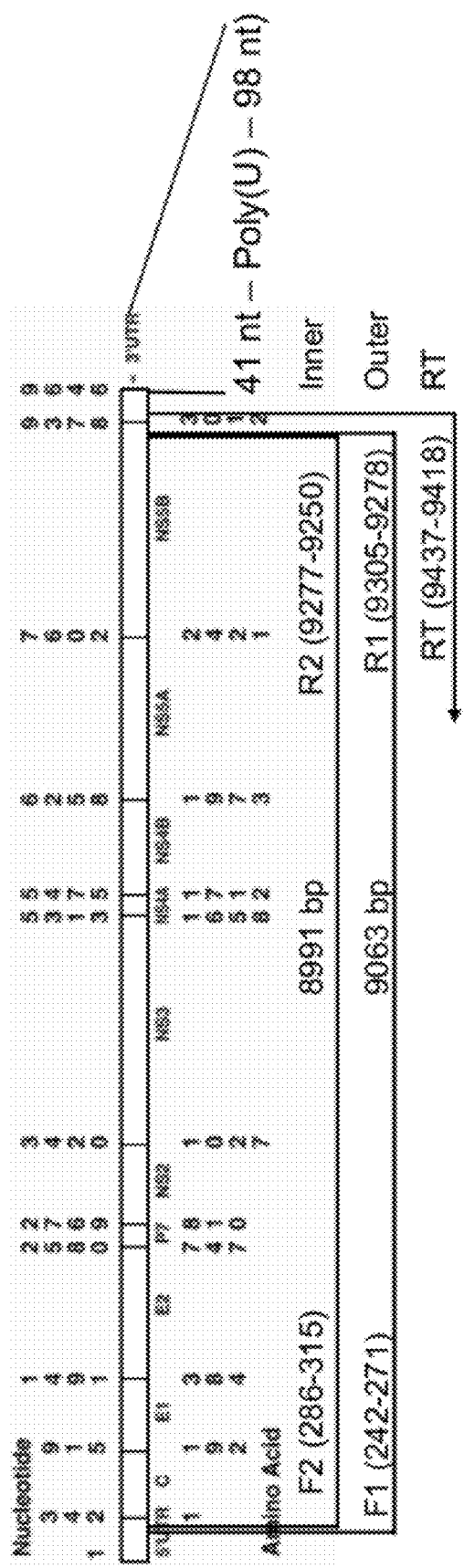
FIG. 2 is a schematic drawing showing HCV genome and primer positions in one embodiment of the invention.

For HCV genotype 1A, GEN1.F1 and GEN1A.R1 were employed, and for HCV genotype 1B, GEN1.F1 and GEN1B.R1 were employed. Specific primers positions are shown in FIG. 2. The PCR reaction was incubated at 94° C. for 2 min, followed by 30 cycles at 94° C. for 15 sec, 68° C.−0.5° C./cycle ('touchdown' PCR) for 20 sec, and 68° C. for 12 min, and followed by incubation at 68° C. for 12 min. The completed PCR reaction was diluted 1:10 into the second PCR reaction (50 µl), with the same composition and PCR cycling parameters as in the first PCR reaction, except 3.2 units Klentaq DNA polymerase, 1.6 units of Pfu DNA polymerase, and nested primers were utilized (for HCV genotype 1A: GEN1.F2: and GEN1A.R2; for HCV genotype 1B:

GEN1.F2 and GEN1B.R2:). The DNA from this PCR (approximately 8991 bp) was purified using the QIAquick 96 PCR Purification kit (Qiagen, CA), and was analyzed by an agarose gel electrophoresis and quantified on a UV Spectrometer U-64 (Beckman).

TA Cloning of Amplicons

PCR products were prepared as described above using Oligo d(A) as an RT primer; and GEN1.C1.F2 and GEN1A.C1.R2 as the inner primers for HCV genotype 1a, or GEN1.C1.F2 and GEN1B.C1.R2 as the inner primers for HCV genotype 1b. The prepared PCR products were electrophoresed at 80V on a 0.8% agarose gel. The agarose gel was prepared with 1.2 μg crystal violet per 1 ml of TAE buffer used in gel preparation. The gel was visualized using a 'visible light' light box. Appropriately sized bands representing the ~8991 bp product were excised from the gel. DNA was isolated from the gel slices using a standard gel extraction kit (e.g., QIAquick Gel Extraction Kit, Qiagen, Catalog #28704). Purified products were inserted in the pCR®-XL-TOPO® vector (Invitrogen, CA, USA). Plasmid was electroporated into electrocompetent E. coli, cultured in SOC media for 1 hour at 36° C., and then cultured with Luria broth containing 50 μg Kanamycin as a selective agent per milliliter Luria broth.

Figure 3:
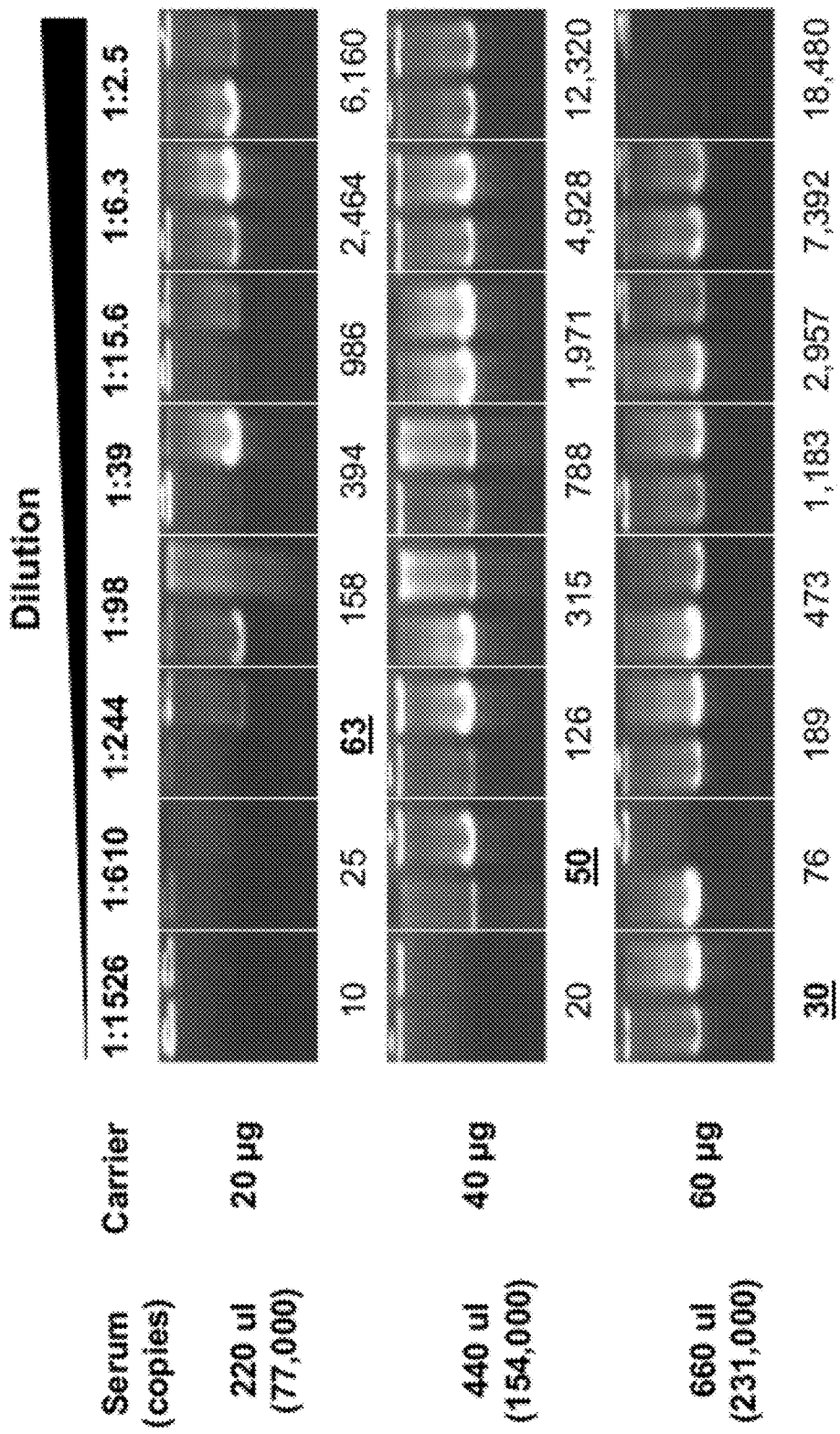
FIGS. 3 and 4 show electrophoreses images illustrating sensitivity of an RT-PCR method of the invention.

2. Results:

2.1 Determination of the Sensitivity of the RT-PCR Assay Using Dilutions of HCV RNA In this study, the estimated sensitivity of the RT-PCR method described herein, using the RNA isolated from HCV-infected plasma (Promax), was determined RNA was isolated from 220, 330 and 660 ul of plasma, with different amounts of carrier RNA. In order to determine the relative detection limits (expressed as number of HCV copies/reaction), the isolated RNA was diluted for RT-PCR as shown in FIG. 3. When 220 μl of plasma with 20 ug of poly(rA) carrier RNA was used, the sensitivity was about 63 copies/reaction. However, RT-PCR band densities varied, implying that either poly(rA) carrier RNA or the amount of HCV RNA in the specimen, was not optimal. When 440 μl of plasma with 40 μg of poly(rA) carrier RNA was used, the sensitivity was about 50 copies/reaction. In addition, the band densities were consistent. When 660 μl of plasma with 60 μg of poly(rA) carrier RNA was used, the sensitivity was better than 30 copies/reaction. Although the 660 μl of plasma with 60 μg carrier RNA gave the best sensitivity, a 2.5-fold dilution did not yield a RT-PCR product, suggesting a possible inhibitory substance was present in the sample. Further analysis has indicated that 40 μg of carrier RNA with 660 ul of plasma yields the best results (data not shown). It is noted that the copy numbers in the FIG. 3 was calculated based 100% recovery from Qiagen column, while, in practice, the recovery efficiency is around 80%. Therefore, the sensitivity of RT-PCR step can be estimated as 50, 40 and 24 copies/reaction, respectively.

2.2 Determination of the Best Carrier RNAs for HCV RNA Isolation

The carrier RNA used in the HCV viral RNA isolation, poly(rA), provided with the Qiagen kit, may influence RT-PCR due to the its complementarity to the poly(U) region. Different RNAs with potential as carrier RNA, including in poly(rA), bacterial tRNA, and bacterial ribosomal RNA, were tested to determine which can serve as the best carrier RNA for the RT-PCR method described herein (see FIG. 4 and discussions in section 2.3). The results indicated that bacterial ribosomal RNA (data not shown) is less suitable than bacterial tRNA and poly(rA) in this assay. When poly(rA) was used as carrier RNA, there were no significant differences in HCV RNA yield with 20, 40 or 60 μg of carrier, whereas with tRNA, the yields of HCV RNA increased with increasing amounts of carrier, as assessed by qRT-PCR (see Table 2). Consistently, the RT-PCR results confirmed that the amount of 60 μg/column tRNA is better than that of 40 μg/column (see FIG. 4 and discussions in section 2.3). Although the copy numbers of HCV molecules isolated from plasma are similar between carrier RNAs, e.g. 40 μg/column poly(rA) and 60 μg/column bacterial tRNA, the RT-PCR results indicate an improved yield of PCR product if bacterial tRNA was used as carrier RNA, presumably due to interference with the RT reaction by poly(rA).

TABLE 2

Effect of the amount of carrier RNA on HCV RNA isolation

| Plasma (16400 IU/ml) | Carrier RNA | CT volume from qRT-PCR | |
|---|---|---|---|
| | | Poly(rA) | tRNA |
| 220 ul (isolation A) | 20 μg/column | 27.41 | 28.22 |
| 220 ul (isolation B) | 40 μg/column | 27.29 | 27.67 |
| 220 ul (isolation C) | 60 μg/column | 27.41 | 27.27 |
| Difference | B − A | −0.12 | −0.55 |
| | C − A | −0.13 | 0.40 |

2.3 Determination of the Sensitivity of the RT-PCR Assay Using Dilutions of HCV-Infected Serum.

Figure 4:
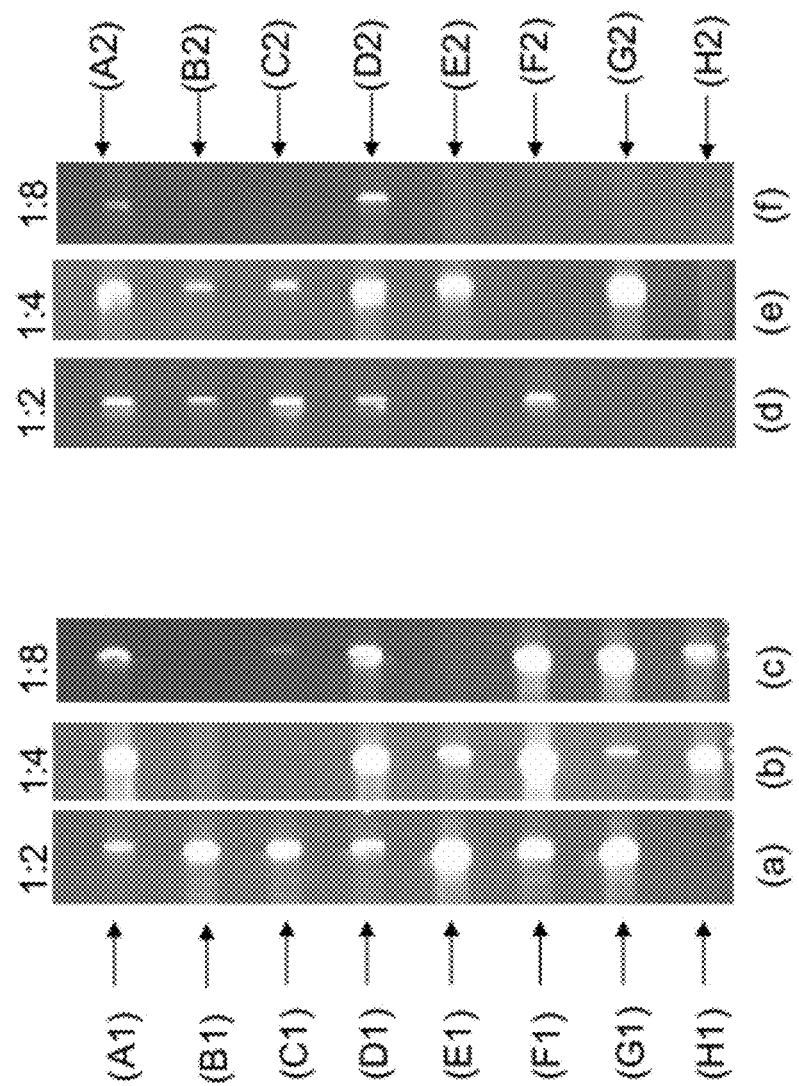

In section 2.1, the RT-PCR sensitivity can be as low as 24 copies/reaction, based on series of diluted RNA isolated from HCV-infected serum. To determine the sensitivity of the method using the RNA isolated from low-titer specimens, HCV-infected plasma samples were diluted with healthy donor plasma, and RNA isolated as described previously. As shown in FIG. 4, the HCV-infected plasma was diluted to as low as 820 IU/ml to isolate viral RNA in the presence of different carrier RNAs. The isolated RNA was diluted 1:2, 1:4, and 1:8, and then the RT-PCR method was performed as described herein. When the sample was diluted to 820 IU/ml, 1 out of 3 samples were amplified by RT-PCR from 1:2 diluted RNA, while 2 out of 3 was amplified by RT-PCR from 1:4 diluted RNA (see FIG. 4). In all of the samples shown in FIG. 4(a)-4(f), the volume of the plasma for RNA isolation was 660 μL (which approximately corresponded to 50× dilution of HCV-positive plasma for samples A1-H1 and A2-D2, to 200× dilution of HCV-positive plasma for samples E2-G2; and the diluent, the healthy donor plasma, as—negative control for sample H2). The HCV concentration of each of samples A1-H1 and A2-D2 was about 3280 IU/mL. The HCV concentration of each of samples E2-G2 was about 820 IU/mL. The diluted plasma samples were then used to isolate viral RNA as described above in the presence of a carrier RNA. In FIGS. 4(a)-4(c), samples A1-D1 show the results where 40 μg of tRNA was used as the carrier RNA, and samples E1-H1 where 60 μg of tRNA was used as the carrier RNA. In FIGS. 4(d)-4(f), samples A2-D2 show the results where 40 μg of Poly-A was used as the carrier RNA; samples E2-H2 show the results where 40 μg of tRNA was used as the carrier RNA. The isolated HCV RNA for the samples in FIGS. 4(a) and 4(d), FIGS. 4(b) and 4(e), and FIGS. 4(c) and 4(f) was diluted 1:2, 1:4 and 1:8, respectively, and then RT-PCR of the diluted HCV RNA samples was performed as described above. As shown in FIG. 4, the results indicate that even a four-fold dilution of serum containing 820 IU/ml HCV can successfully be used in the RT-PCR assay. Therefore, the sensitivity of this novel method could be equal or less than 820 IU/ml. It is believed that a further improvement in sensitivity could be achieved, because, as described in the section above, 60 μg/ml carrier tRNA give improved results over 40 μg/ml carrier tRNA.

2.4 The RT-PCR Assay Success Rate is Over 90% for Both Genotype 1a and 1b.

To assess the performance of the newly developed method, particularly whether the method can be applied to different HCV 1a/1b isolates, plasma samples from clinical trials were investigated. The results are summarized in Table 3 below. For example, the titer of the plasma samples ranged from 890 IU/ml to greater than 10e7 IU/ml. For samples with titer greater than or equal to 50,000 IU/ml, 220 ul of plasma was used, and for samples with titer less than 50,000 IU/ml, 660 ul of plasma was used. As shown in Table 3, the HCV genome was successfully amplified using the RT-PCR methods described herein, and further sequenced, with a greater than 90% success rate. Although there were some failed samples, there seems little correlation of this failure to the virus titer, which indicates sensitivity of RT-PCR is not the reason for the failure. Since there is no sequence from the failed samples, a possible reason for failure may be due to incorrect genotyping.

TABLE 3

Summary of the study of clinical samples

| Numbers of clinical samples | Genotype | Titer Range (IU/ml) | Successful rate for RT-PCR (%) | Successful rate for sequence (%) |
|---|---|---|---|---|
| 1,800 | 1a | Low (approx. $10^3$-$5 \times 10^4$) | 95% | 94% |
| 3,600 | 1a | High (>approx. $5 \times 10^4$) | 98% | 97% |
| 800 | 1b | Low (approx. $10^3$-approx. $5 \times 10^4$) | 95% | 94% |
| 1,600 | 1b | High (>approx. $5 \times 10^4$) | 98% | 97% |

2.5 Sequence Analysis of TA Cloned Produced of RT-PCR Amplicons

To determine the fraction of clones that include HCV inserts, both vector primers and sequencing primers specific to the NS3 protease were used. On average, 90% of clones from each cloning reaction contained the target insert.

The results shown above indicate that the RNA isolation, RT, and PCR described above can be effectively employed in a majority of patients infected with HCV genotypes 1a and 1b, and enables the analysis of genetic diversity of HCV isolates.

While a number of embodiments and examples of the present invention are described herein, it is apparent that these embodiments and examples may be altered to provide additional embodiments and examples which utilize the pharmaceutical formulations and drug regimens of this invention. Therefore, it will be appreciated that the scope of the present invention is to be defined by the appended claims rather than by the specific embodiments that have been represented by way of example above.

What is claimed is:

1. A method of amplifying a hepatitis C virus (HCV) nucleic acid from an HCV infected sample, comprising amplifying a segment of a DNA template complementary to a genome of HCV RNA from the sample by a two-stage polymerase chain reaction (PCR), wherein a first stage PCR employs a first outer primer and a second outer primer, and a second stage PCR employs a first inner primer and a second inner primer, wherein:

i) the nucleotide sequence of the first outer primer consists of the nucleotide sequence as set forth in SEQ ID NO: 9:

(SEQ ID NO: 9)
        5'-CAAGACTGCTAGCCGAGTAGTGTTGGGTCG-3';
        and ii) the nucleotide sequence of the second outer primer consists of the nucleotide sequence as set forth in SEQ ID NO: 10 or SEQ ID NO: 11:

(SEQ ID NO: 10)
        5'-CCGGGCAYGAGACACGCTGTGATAAATG-3',
        or (SEQ ID NO: 11)
        5'-TCGGGCACGAGACAVGCTGTGATATATG-3', wherein Y is C, T or U; and V is A, C or G;

iii) the nucleotide sequence of the first inner primer consists of the nucleotide sequence as set forth in SEQ ID NO: 12 or SEQ ID NO: 15:

(SEQ ID NO: 12)
        5'-GTACTGCCTGATAGGGTGCTTGCGAGTGCC-3'
        or (SEQ ID NO: 15)
        5'-AAGTACTGCCTGATAGGGTGCTTGCGAGTGCC-3';
        and iv) the nucleotide sequence of the second inner primer consists of the nucleotide sequence as set forth in SEQ ID NO: 13, SEQ ID NO: 14, SEQ ID NO: 16, or SEQ ID NO: 17:

```
5'-TCTCCCCCGCTGTAGCCAGCCGTGAACC-3',    (SEQ ID NO: 13)

5'-TCTCCCCCGCTGTARCCAGCRACGAACC-3',    (SEQ ID NO: 14)

5'-ATCTCCCCCGCTGTAGCCAGCCGTGAACC-3',   (SEQ ID NO: 16)
or
5'-ATCTCCCCCGCTGTARCCAGCRACGAACC-3',   (SEQ ID NO: 17)
``` wherein R is A or G;
wherein the amplified HCV nucleic acid has greater than 8,000 base pairs.

2. The method of claim 1, wherein the HCV nucleic acid is genotype 1a or 1b.

3. The method of claim 2, wherein the HCV nucleic acid is genotype 1a.

4. The method of claim 3, wherein
a) the nucleotide sequence of first outer primer consists of the nucleotide sequence as set forth in SEQ ID NO: 9;
b) the nucleotide sequence of the second outer primer consists of the nucleotide sequence as set forth in SEQ ID NO: 10;
c) the nucleotide sequence of the first inner primer consists of the nucleotide sequence as set forth in SEQ ID NO: 12; and
d) the nucleotide sequence of the second inner primer consists of the nucleotide sequence as set forth in SEQ ID NO: 13.

5. The method of claim 3, wherein
a) the nucleotide sequence of first outer primer consists of the nucleotide sequence as set forth in SEQ ID NO: 9;
b) the nucleotide sequence of the second outer primer consists of the nucleotide sequence as set forth in SEQ ID NO: 10;
c) the nucleotide sequence of the first inner primer consists of the nucleotide sequence as set forth in SEQ ID NO: 15; and
d) the nucleotide sequence of the second inner primer consists of the nucleotide sequence as set forth in SEQ ID NO: 16.

6. The method of claim 2, wherein the HCV nucleic acid is genotype 1b.

7. The method of claim 6, wherein
a) the nucleotide sequence of first outer primer consists of the nucleotide sequence as set forth in SEQ ID NO: 9;
b) the nucleotide sequence of the second outer primer consists of the nucleotide sequence as set forth in SEQ ID NO: 11;
c) the nucleotide sequence of the first inner primer consists of the nucleotide sequence as set forth in SEQ ID NO: 12; and
d) the nucleotide sequence of the second inner primer consists of the nucleotide sequence as set forth in SEQ ID NO: 14.

8. The method of claim 6, wherein
a) the nucleotide sequence of first outer primer consists of the nucleotide sequence as set forth in SEQ ID NO: 9;
b) the nucleotide sequence of the second outer primer consists of the nucleotide sequence as set forth in SEQ ID NO: 11;
c) the nucleotide sequence of the first inner primer consists of the nucleotide sequence as set forth in SEQ ID NO: 15; and
d) the nucleotide sequence of the second inner primer consists of the nucleotide sequence as set forth in SEQ ID NO: 17.

9. The method of claim 1, further comprising the step of forming the DNA template complementary to a genome of HCV RNA from the sample by reverse transcription (RT) using an RT primer, wherein the RT primer comprises a nucleotide sequence of SEQ ID NO: 8 at its 3' end:

```
5'-AAAAAAAAAAAAAAAAAAAA-3'.           (SEQ ID NO: 8)
```

10. The method of claim 1, wherein the DNA template amplification step comprises i) amplifying a segment of the DNA template by the first PCR to produce first amplicons; and ii) amplifying at least a portion of the first amplicons by the second PCR to produce second amplicons that include the amplified HCV nucleic acid.

11. A method of assaying a hepatitis C virus (HCV) nucleic acid in an HCV infected sample, comprising:
a) amplifying a DNA template complementary to a genome of HCV RNA from the sample by a two-stage polymerase chain reaction (PCR) according to claim 1 to produce amplified HCV nucleic acid; and
b) sequencing the amplified HCV nucleic acid.

12. A method of assaying a hepatitis C virus (HCV) nucleic acid in an HCV infected sample, comprising:
a) amplifying a DNA template complementary to a genome of HCV RNA from the sample by a two-stage polymerase chain reaction (PCR) according to claim 1 to produce an amplicon;
b) cloning the amplicon; and
c) sequencing the HCV nucleic acid of the cloned amplicon.

13. A method of monitoring a resistance profile of a patient infected with HCV, comprising:
a) obtaining an HCV infected sample from the patient;
b) amplifying a DNA template complementary to a genome of HCV RNA from the sample by a two-stage polymerase chain reaction (PCR) according to claim 1; and
c) sequencing the amplified HCV nucleic acid.

14. The method of claim 9, where the HCV RNA is primed with the RT primer at a 3' untranslated region (3' UTR) of the genome of the HCV RNA.

15. The method of claim 1, wherein the amplified HCV nucleic acid comprises genes that encode C, E1, E2, NS2, NS3, NS4A, NS4B, NS5A and NS5B proteins.

16. The method of claim 15, wherein the first inner and outer primers independently are primed at a 5' untranslated region (5' UTR) of the HCV RNA genome, and the second inner and outer primers independently are primed at a NS5B region of the HCV RNA genome.

17. The method of claim 1, wherein the first stage PCR is followed by the second stage PCR, and during each of the first and second stage PCRs, each PCR reaction mixture independently is incubated
a) at temperature T1 for time period R1, and
b) subsequently followed by a plurality of touchdown PCR cycles, each touchdown cycle comprising incubation of the PCR reaction mixture
i) at temperature T2 for time period R2,
ii) subsequently at a temperature of $[T3-(V°C.×m)]$ for $m^{th}$ cycle for time period R3, and
iii) subsequently at temperature T4 for time period R4, wherein:
T1 and T2 independently are in a range of between 90° C. and 100° C.;
T3 and T4 independently are in a range of between 65° C. and 70° C.;
R1 is in a range of between 1 minute and 5 minutes;
R2 is in a range of between 5 seconds and 45 seconds;
R3 is in a range of between 10 seconds and 40 seconds;
R4 is in a range of between 5 minutes and 20 minutes; and
V is in a range of between 0.2° C. and 0.8° C.

18. The method of claim 17, wherein
R1 is in a range of between 1 minute and 3 minutes;
R2 is in a range of between 10 seconds and 20 seconds;
R3 is in a range of between 15 seconds and 25 seconds;
R4 is in a range of between 8 minutes and 15 minutes; and
the number of touchdown PCR cycles is in a range of between 20 and 50.

19. The method of claim 1, wherein the amplified HCV nucleic acid is produced with greater than 80% reproducibility.

20. The method of claim 11, wherein the amplified HCV nucleic acid is produced with greater than 80% reproducibility.

21. The method of claim 12, wherein the amplified HCV nucleic acid is produced with greater than 80% reproducibility.

* * * * *